US008912392B2

(12) United States Patent
Lyznik et al.

(10) Patent No.: US 8,912,392 B2
(45) Date of Patent: Dec. 16, 2014

(54) METHODS FOR ALTERING THE GENOME OF A MONOCOT PLANT CELL

(75) Inventors: L. Aleksander Lyznik, Johnston, IA (US); Yumin Tao, Fremont, CA (US); Huirong Gao, Johnston, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 1144 days.

(21) Appl. No.: 12/147,834

(22) Filed: Jun. 27, 2008

(65) Prior Publication Data

US 2009/0133152 A1 May 21, 2009

Related U.S. Application Data

(60) Provisional application No. 60/947,003, filed on Jun. 29, 2007, provisional application No. 61/033,150, filed on Mar. 3, 2008.

(51) Int. Cl.
*C12N 15/87* (2006.01)
*C12N 15/82* (2006.01)
*C12N 9/22* (2006.01)

(52) U.S. Cl.
CPC .............. *C12N 15/8213* (2013.01); *C12N 9/22* (2013.01)
USPC ....................................... 800/278; 800/320.1

(58) Field of Classification Search
None
See application file for complete search history.

(56) References Cited

U.S. PATENT DOCUMENTS

| | | | |
|---|---|---|---|
| 5,527,695 A | 6/1996 | Hodges et al. | |
| 5,567,600 A | 10/1996 | Adang et al. | ............... 536/23.71 |
| 5,744,336 A | 4/1998 | Hodges et al. | |
| 5,792,632 A | 8/1998 | Dujon et al. | |
| 5,910,415 A | 6/1999 | Hodges et al. | |
| 5,981,840 A * | 11/1999 | Zhao et al. | .................... 800/294 |
| 6,110,736 A | 8/2000 | Hodges et al. | |
| 6,114,600 A | 9/2000 | Ow et al. | |
| 6,410,329 B1 | 6/2002 | Hansen et al. | |
| 6,528,313 B1 | 3/2003 | Le Mouellic et al. | |
| 6,528,314 B1 | 3/2003 | Le Mouellic et al. | |
| 6,610,545 B2 | 8/2003 | Dujon et al. | |
| 6,638,768 B1 | 10/2003 | Le Mouellic et al. | |
| 6,746,870 B1 | 6/2004 | Ow et al. | |
| 6,781,032 B1 | 8/2004 | Gruissem et al. | |
| 7,060,499 B1 | 6/2006 | Saito et al. | |
| 7,098,031 B2 | 8/2006 | Choulika et al. | |
| 7,126,041 B1 | 10/2006 | Helmer et al. | |
| 7,135,608 B1 | 11/2006 | O'Gorman et al. | |
| 7,285,538 B2 | 10/2007 | Choulika et al. | |
| 7,351,877 B2 | 4/2008 | Suttie et al. | |
| 7,476,539 B2 | 1/2009 | Saito et al. | |
| 7,566,814 B2 | 7/2009 | O'Gorman et al. | |
| 7,598,365 B2 | 10/2009 | D'Halluin et al. | |
| 7,608,761 B2 | 10/2009 | Baley et al. | |
| 7,632,985 B2 | 12/2009 | Malven et al. | |
| 7,736,886 B2 | 6/2010 | Puchta et al. | |
| 7,897,372 B2 | 3/2011 | Duchateau et al. | |
| 2002/0107214 A1 | 8/2002 | Choulika et al. | |
| 2002/0123145 A1 | 9/2002 | Ow | |
| 2004/0019002 A1 | 1/2004 | Choulika et al. | |
| 2004/0203153 A1 | 10/2004 | Le Mouellic et al. | |
| 2004/0250301 A1 | 12/2004 | Mouellic et al. | |
| 2005/0172365 A1 | 8/2005 | Puchta et al. | |
| 2006/0206949 A1 | 9/2006 | Arnould et al. | |
| 2006/0253918 A1 | 11/2006 | Que | |
| 2006/0282911 A1 | 12/2006 | Bull et al. | |
| 2006/0282914 A1 | 12/2006 | D'Halluin | |
| 2006/0288444 A1 | 12/2006 | McCarroll et al. | |
| 2007/0117128 A1* | 5/2007 | Smith et al. | ....................... 435/6 |
| 2008/0083042 A1 | 4/2008 | Butruille et al. | |
| 2009/0031438 A1 | 1/2009 | Kennard et al. | |
| 2009/0286320 A1 | 11/2009 | O'Gorman et al. | |

FOREIGN PATENT DOCUMENTS

| | | |
|---|---|---|
| AR | 067358 | 10/2009 |
| CA | 2691440 | 1/2009 |
| CN | 101849010 | 9/2010 |
| EP | 0 317 509 A2 | 5/1989 |
| EP | 0469273 | 2/1992 |
| EP | 0 682 112 A1 | 11/1995 |
| EP | 0602899 | 10/2004 |
| EP | 1476547 | 12/2006 |
| EP | 1689870 | 12/2008 |
| EP | 2167666 | 3/2010 |
| EP | 2568048 | 3/2013 |
| WO | WO 98/32326 | 7/1998 |
| WO | WO 98/49332 | 11/1998 |
| WO | WO 99/55851 A2 | 11/1999 |
| WO | WO 00/12734 | 3/2000 |
| WO | WO 0046386 | 8/2000 |

(Continued)

OTHER PUBLICATIONS

Seibert, R., and Puchta, H., Efficient Repair of Genomic Double-Strand breaks by Homologous Recombinatuion between Directly Repeated Sequences in the Plant Genome, 2002 Plant Cell 14:1121-1131.*
Lloyd et al 2005 PNAS 102:6 p. 2232-2237.*
Wehrkamp-Richter S et al., Abstract P-17: I-SceI-stimulated intrachromosomal homologous recombination in maize, (2006), XP002501443.
University of Warwick, UK, Poster Abstracts Meiosis and the Causes and Consequences of Recombination, URL:http://www.boichemsitry.org/meetings/postertoc.SA049/default.htm (2006) XP002501444.
Srivastava Vibha et al., Cre-mediated site-specific gene integration for consistent transgene expression in rice, Plant Biotechnology Journal, (Mar. 2004) vol. 2, No. 2 pp. 169-179, XP002501441.

(Continued)

Primary Examiner — David T Fox
Assistant Examiner — Matthew Keogh
(74) Attorney, Agent, or Firm — Ballard Spahr LLP

(57) ABSTRACT

Methods and compositions for altering the genome of a monocot plant cell, and a monocot plant are disclosed. The methods and compositions use a double-strand break inducing agent to alter a monocot plant or plant cell genomic sequence comprising a recognition sequence for the double-strand break inducing agent.

4 Claims, 17 Drawing Sheets

(56) References Cited

FOREIGN PATENT DOCUMENTS

| WO | WO 01/11058 A1 | 2/2001 |
|---|---|---|
| WO | WO 01/23545 A1 | 4/2001 |
| WO | WO 03/004659 | 1/2003 |
| WO | WO 03025183 | 3/2003 |
| WO | WO 03038104 | 5/2003 |
| WO | WO 03074700 | 9/2003 |
| WO | WO 03078619 | 9/2003 |
| WO | WO 2004/015134 A2 | 2/2004 |
| WO | WO 2004031346 | 4/2004 |
| WO | WO 2004067736 | 8/2004 |
| WO | WO 2004067753 | 8/2004 |
| WO | WO 2005049842 * | 6/2005 |
| WO | WO 2005105989 | 11/2005 |
| WO | WO 2006074956 | 7/2006 |
| WO | WO 2006097784 | 9/2006 |
| WO | WO 2006097853 | 9/2006 |
| WO | WO 2006097854 | 9/2006 |
| WO | WO 2006/107954 | 10/2006 |
| WO | WO 2006105946 | 10/2006 |
| WO | WO 2007/034262 | 3/2007 |
| WO | WO 2007/047859 A2 | 4/2007 |
| WO | WO 2008021207 | 2/2008 |
| WO | WO 2008037436 | 4/2008 |
| WO | WO 2008093152 | 8/2008 |
| WO | WO 2008145731 | 12/2008 |
| WO | WO 2008148559 | 12/2008 |
| WO | WO 2009/006297 | 1/2009 |
| WO | WO 2009114321 | 9/2009 |

OTHER PUBLICATIONS

Katleen M J Butaye et al. Approaches to Minimize Variation of Transgene Expression in Plants, Molecular Breeding, vol. 16 No. 1, Aug. 1, 2005, pp. 79-91, XP019258738.

Kathleen D'Halluin et al, Homologous recombination: a basis for targeted genome optimization in crop species such as maize, Plant Biothechnology Journal, Jan. 2008, vol. 6 No. 1, pp. 93-102 XP002501442.

Jean-Charles Epinat, A Novel Engineered Meganuclease Induces Homologous Recombination in Yeast and Mammalian Cells, Nucleic Acids Research, 2003, vol. 31, No. 11.

Holger Puchta, The Repair of Double-Strand Breaks in Plants; Mechanisms and Consequences for Genome Evolution, Journal of Experimental Botany,Jan. 2005, vol. 56, No. 409, pp. 1-14.

Holger Puchta et al., Homologous Recombination in Plant Cells is Enhanced by In Vivo Induction of Double Strand Breaks into DNA by a Site-Specific Endonuclease, Nucleic Acids Research, 1993, vol. 21, No. 22.

Ralph Siebert et al., Efficient Repair of Genomic Double-Strand Breaks by Homologous Recomination between Directly Repeated Sequences in the Plant Genome, The Plant Cell, May 2002, vol. 14, pp. 1121-1131.

Michael Pacher et al., Two Unlinked Double-Strand Breaks Can Induce Reciprocal Exchanges in Plant Genomes via Homologous Recombination and Nonhomologous End Joining, Genetics, 2007.

N. Guhan et al., Structural and Functional Characteristics of Homing Endonucleases, Critical Reviews in Biochemistry and Molecular Biology, 2003, 38(3): 199-248.

Matthew H.Porteus et al., Gene Targetinig Using Zinc Finger Nucleases, Nature Biotechnology, Aug. 2005, vol. 23, No. 8.

Michal Szczepek et al., Structure-Based Redesign of the Dimerization Interface Reduces the Toxicity of Zinc-Finger Nucleases, Nature Biotechnology, Jul. 2007, vol. 25, No. 7.

Jeffrey C. Miller et al., An Improved Zinc-Finger nuclease Architecture for Highly Specific Genome Editing, Nature Biotechnology, Jul. 2007, vol. 25, No. 7.

Patrick Chames et al., In Vivo selection of Engineered Homing Endonucleases Using Double-Strand Break Induced Homologous Recombiniation, Nucleic Acids Reseach, 2005, vol. 33, No. 20.

Julianne Smith et al., A Combinatorial Approach to Create Artificial Homing Endonucleases Cleaving Chosen Sequences, Nucleic Acids Research, 2006, vol. 34, No. 22.

Yikang S. Rong et al., Targeted Mutagenesis by Homologous Recombination in *D. Melanogaster*, www.genesdev.org, Jun. 12, 2008.

Marina Bibikova et al., Targeted Chromosomal Cleavage and Mutagenesis in *Drosophila* Using Zinc-Finger Nuceases, Genetics, Jul. 2002, 161: 1169-1175.

Kelly Beumer et al., Efficient Gene Targeting in *Drosophila* With Zinc-Finger Nucleases, Genetics, Apr. 2006, 172: 2391-2403.

Lenny Seligman et al., Mutations Altering the Cleavage Specificity of a Homing Endonuclease, Nucleic Acids Research, 2002, vol. 30, No. 17.

M. S. Jurica et al., Homing Endonucleases: Structure, function and evolution, CMLS ,1999, 55: 1304-1326.

Barry L. Stoddard, Homing Endonuclease Structure and Function, Quarterly Reviews of Biophysics 38, 2006, pp. 49-95.

Patrick Lucas et al., Rapid Evolution of the DNA-Bonding site in LAGLIDADG Homing Endonucleases, Nucleic Acids Research, 2001, vol. 29, No. 4.

Chris Allen et al., The Mutagenic potential of a single DNA Double-Strand Break in a Mammalian Chromosome is Not Influenced by Transcription, www.sciencedirect.com, DNA repair 2 (2003), 1147-1156.

Nadiya Orel et al., Different Pathways of Homologous Recombination Are Used for the Repair of Double-Strand Breaks Within Tandemly Arranged Sequences in the Plant Genome, The Plant Journal, 2003, 35, 604-612.

Mary-Dell M. Chilton et al., Targeted Integration of T-DNA into the Tobacco Genome at Double-Stranded Breaks: New Insights on the Mechanism of T-DNA Integration, Plant Physiology, Nov. 2003, vol. 133, pp. 956-965.

Laura E. Rosen et al., Homing endonuclease I-CreI Derivatives with Novel DNA Target Specificities, Nucleic Acids Research, 2006, vol. 17, pp. 4791-4800.

George Silva et al., Analysis of the LLAGLIDADG Interface of the Monomeric Homing Endonuclease I-DmoI, Nucleic Acids Research, 2004, vol. 32, No. 10.

Francine B. Perler, InBase, The Intein Database, Nucleic Acids Research, 2000, vol. 28, No. 1.

J. Peter Gogarten et al., Inteims: Structure, Function, and Evolution, Annuu. Rev. Microbiol, 2002, 56:263-287.

Carmen M. Moure et al., Crystal Structure of the Intein Homing Endonuclease PI-SceI Bound to its Recognition Sequence, Nature Structural Biology, Oct. 2002, vol. 9, No. 10.

Zhiei Chen et al., A Highly Sensitive Selection Method for Directed Evolution of Homing Endonucleases, Nucleic Acids Research, 2005, vol. 33, No. 18.

Tzvi Tzfira et al., Site-Specific Integration of *Agrobacterium tumefaciens* T_DNA Via Double-Stranded Intermediates, Plant Physiology, Nov. 2003, vol. 133, pp. 1011-1023.

Vera Gorbunova et al., Non-Homologous DNA End Joining in Plant Cells is Associated with Deletions and Filler DNA Insertions, Nucleic Acids Research, 1997, vol. 25., No. 22.

Palaniyandi Manivasakam et al. Restriction Enzymes Increase Efficiencies of Illegitimate DNA Integration But Decrease Homologous Integration in Mammalian Cells, Nucleic Acids Research, 2001, vol. 29, No. 23.

Yikang S Rong et al., Gene Targeting by Homologous Recombination in *Drosophila*, www.sciencemag.org, Jun. 2000 vol. 288.

Tzvi Tzfira et al., Site-Specific Integration of *Agrobacterium tumefaciens* T-DNA via Double-Stranded Intermediates, Plant Physiology, Nov. 2003, vol. 133, pp. 1011-1023.

Mathias Gruen et al., An In Vivo Selection System for Homing Endonuclease Activity, Nucleic Acids Research, 2002, vol. 30, No. 7.

Alan Lloyd et al., Targeted Mutagenesis Using Zinc-Finger Nucleases in *Arabidopsis*, PNAS, Feb. 8, 2005, vol. 102, No. 6, pp. 2232-2237.

Alexander E. Smith et al., Specific Targeting of Cytosine Methylation to DNA Sequences in Vivo, Nucleic Acids Research, 2206, vol. 00, No. 00 1-15.

Kaplinsky, et al., "Utility and distribution of conserved noncoding sequences in the grasses," *PNAS*, 99: pp. 6147-6151 (2002).

Kim, et al., "Transgene structures in T-DNA-inserted rice plants," *Plant Mol Biol*, 52: pp. 761-773 (2003).

(56) References Cited

OTHER PUBLICATIONS

Kumar and Fladung, "Transgene integration in aspen: structures of integration sites and mechanisms of T-DNA integration," *Plant J*, 31(4): pp. 543-551 (2002).

"Red/ET Recombination: Cloning Without Restriction Enzymes," Gene Bridges, Available at: <http://www.genebridges.com/gb/courses.php>.

Stougaard, "Substrate-dependent negative selection in plants using a bacterial deaminase gene," *Plant J*, 3(5): pp. 755-761 (1993).

Sung and Klein, "Mechanism of homologous recombination: mediators and helicases take on regulatory functions," *Nature Reviews Mol Cell Biol*, 7: pp. 739-750 (2006).

Truett, et al., "Preparation of PCR-quality mouse genomic DNA with hot sodium hydroxide and tris (HotSHOT)," *Bio Techniques*, 29(1): pp. 52-54 (2000).

Uchiyama, et al., "Characterization of plant XRCC1 and its interaction with proliferating cell nuclear antigen," *Planta*, 227(6): pp. 1233-1241 (2008).

Wisman, et al. "The behaviour of the autonomous maize transposable element En/Spm in *Arabidopsis thaliana* allows efficient mutagenesis," *Plant Mol Biol* 37(6): pp. 989-999 (1998).

International Search Report issued Jan. 14, 2009 for PCT/US08/68570, which was filed Jun. 27, 2008 [Inventor—Lyznik, et al.; Applicant—Pioneer Hi-Bred International, Inc.] [6 pages].

Written Opinion issued Dec. 29, 2009 for PCT/US08/68570, which was filed Jun. 27, 2008 [Inventor—Lyznik, et al.; Applicant—Pioneer Hi-Bred International, Inc.] [5 pages].

International Preliminary Report on Patentability issued Jan. 5, 2010 for PCT/US08/68570, which was filed Jun. 27, 2008 [Inventor—Lyznik, et al.; Applicant—Pioneer Hi-Bred International, Inc.] [6 pages].

Extended European Search Report issued Feb. 13, 2013 for European Patent Application No. EP 12192636.4, which was filed Jun. 27, 2008 [Inventor—Lyznik, et al.; Applicant—Pioneer Hi-Bred International, Inc.] [6 pages].

\* cited by examiner

```
T0s                           ↓
ATS-normal    TAGGGATAACAGGGTAATAATAATAGTAAATGGCCCACAGCAAGCACGGCC
ATST0-250     TAGGGAT::::::::::::::::::::::::::::::::::::::GCC
ATST0-317     TAGGGATA:CAGGGTAATAATAATAGTAAATGGCCCACAGCAAGCACGGCC
ATST0-310     TAGGGATAA::GGGTAATAATAATAGTAAATGGCCCACAGCAAGCACGGCC
ATST0-3D10    TAGGGATAA:::::::::::TAATAGTAAATGGCCCACAGCAAGCACGGCC
ATST0-5E9     TAGGGATA::::GGTAATAATAATAGTAAATGGCCCACAGCAAGCACGGCC
ATST0-9C11    TAGGGA:::CAGGGTAATAATAATAGTAAATGGCCCACAGCAAGCACGGCC
ATST0-B9      TAGGGAT::CAGGGTAATAATAATAGTAAATGGCCCACAGCAAGCACGGCC
ATST0-D9      TAGGGATAA:::::::::::::::::TGcCCCACAGCAAGCACGGCC
ATST0-C6      TAGGGATA:CAGGGTAATAATAATAGTAAATGGCCCACAGCAAGCACGGCC
ATST0-1B12    TAGGGATAAaCAGGGTAATAATAATAGTAAATGGCCCACAGCAAGCACGGC
ATST0-4-1     TAGGGAT:::::::::gaccatgaAGTAAATGGCCCACAGCAAGCACGGCC
ATST0-1-3     TAGGG::::CAGGGTAATAATAATAGTAAATGGCCCACAGCAAGCACGGCC
ATST0-11A10
T:::::::::::::::::::::::::AATAATAATAGTAAATGGCCCACAGCAAGCACGGCC T1s
ATS           TAGGGATAACAGGGTAATAATAATAGTAAATGGCCCACAGCAAGCACGGCC
ATST0-250     TAGGGAT::::::::::::::::::::::::::::::::::::::GCC
ATST0-250-2   TAGGGAT::::::::::::::::::::::::::::::::::::::GCC
ATST0-250-5   TAGGGAT::::::::::::::::::::::::::::::::::::::GCC
ATST0-250-6   TAGGGAT::::::::::::::::::::::::::::::::::::::GCC
ATST0-250-9   TAGGGAT::::::::::::::::::::::::::::::::::::::GCC ATST0-317     TAGGGATA:CAGGGTAATAATAATAGTAAATGGCCCACAGCAAGCACGGCC
ATST0-317-2   TAGGGATA:CAGGGTAATAATAATAGTAAATGGCCCACAGCAAGCACGGCC
ATST0-317-6   TAGGGATA:CAGGGTAATAATAATAGTAAATGGCCCACAGCAAGCACGGCC
ATST0-317-7   TAGGGATA:CAGGGTAATAATAATAGTAAATGGCCCACAGCAAGCACGGCC
```

Event 1: Plant 82157663. Clones from MluI cut fragments
TS  GTGCCCCGGCGGAGGATATATATACCTCACACGTACGCGTACGCGTATATATACGTGCGCTGCTACTCATT
    GTGCCCCGGCGGAGGATATATATA::::::::::::::::::::::::::::::TACGTGCGCTGCTACTCATT
    GTGCCCCCCCGGACGGATATATATAC::::::::::::::::::::::::::::::GTGCCCTGCTACTCATT
    GTGCCCCGGCGGAGGATATATATAC::::::::::::::::::::::::::::::*GTGCGCTGCTG*CTCATT Event 2: Plant 82157698. Direct PCR clones with 220bp deletion
TS  GTGCCCCGGCGGAGGATATATATACCTCACACGTACGCGTACGCGTATATATACGTGCGCTGCTACTCATT
    GTGCCCCGGCGGAGGATATATATACCTCAG::::::::::::::::::::::::::::::::::::::::
    ::::::::::::::::::::::::::::::::::::::::::::::::::::::::::::::::::::::
    ::::::::::::::::::::::::::::::::::::::::::::::::::::::::::::::::::::::
    :::::::::::::::::::::::::::::::::::::CGCGGGAGGCAGCTGCTAGCGTTAGCGT Event 3: Plant 82157714. Clones from Lig3-4 cut fragments
TS  GTGCCCCGGCGGAGGATATATATACCTCACACGTACGCGTACGCGTATATATACGTGCGCTGCTACTCATT
    GTGCCCCCGCCGCAGGATATATATACCTCACAC::ACGCGTACGCGTATATATACGTGCGCTGCTACTCATT Event 4: Callus C3. Clones from MluI cut fragments
TS  GTGCCCCGGCGGAGGATATATATACCTCACACGTACGCGTACGCGTATATATACGTGCGCTGCTACTCATT
    GTGCCCCGGCGGAGGATATATATACCTCACAC::::::::::GTATATATACGTGCGCTGCTACTCATT
    GTGCCCCGGCGGAGGA:::::::::::::::::::::::::::TATATATACGTGCGCTGCTACTCATT
    GTGCCCCGGCGGCAGG::::::::::::::::::::::::::::ATATATACGTGCGCTGCTACTCATT
    GTGCCCCGGCGGAGGATACAGCTCAGT::::::::::::::::::::::::::::CTGCTACTCATT Event 5: Callus C7. Clones from MluI cut fragments
TS  GTGCCCCGGCGGAGGATATATATACCTCACACGTACGCGTACGCGTATATATACGTGCGCTGCTACTCATT
    :::::
    :::::::::::::::::::::::::::::::::::::::CGTACGCGTATATATACGTGCGCTGCCACTCATT
    GTGCCCCGGCG:::::::::::::::::::::::::::::::TACCCGTATATATACGTGCGCTGCTACTCATT
    GTGCCCCGGCGGAGGATATATAT::::::::::::::::::GTATATATACGTGCGCTGCTACTCATT Event 6: Callus C12. Clones from MluI cut fragments
TS  GTGCCCCGGCGGAGGATATATATACCTCACACGTACGCGTACGCGTATATATACGTGCGCTGCTACTCATT
    GTGCCCCGGCGGAGGA:::::::::::::::::::::::::::TATATATACGTGCGCTGCTACTCATT Event 7: Callus D2. Clones from LIG3-4 cut fragments
TS  GTGCCCCGGCGGAGGATATATATACCTCACACGTACGCGTACGCGTATATATACGTGCGCTGCTACTCATT
    GTGCCCCGGCGGAGGATATATA::CCTCACACGTACGCGTACGCGTATATATACGTGCGCTGCTACTCATT

```
Event 8: Callus D10. Clones from MluI cut fragments
TS   GTGCCCCGGCGGAGGATATATATACCTCACACGTACGCGTACGCGTATATATACGTGCGCTGCTACTCATT
     GTGCCCCGGCGGAGGA::::::::::::::::::::::::::::TATATATACGTGCGCTGCTACTCATT
     GTGCCCCGGCGGAGGATATATACGTGCGCTGCTACTCATTTGCGCGTATATATACGTGCGCTGCTACTCAT
     GTGCCCCGGCGGAGGATATATATAC::::::::::::::::::::::::GTGCGCTGCTACTCATT
     GTGCCCCGGCGGAGGATATATATACCTCACGATCACCGGCTGCGGAAATATATATACGTGCGCTGCTACTC
     ATT Event 9: Callus D11. Direct PCR clones
TS   GTGCCCCGGCGGAGGATATATATACCTCACACGTACGCGTACGCGTATATATACGTGCGCTGCTACTCATT
     GTGCCCCGGCGGAGGATATATATAC:::::::::::::::::::::::GTGCGCTGCTACTCATT
     GTGCCCCGGCGGAGGATATATATAC:::::::::::::::GCGTATATATACGTGCGCTGCTACTCATT
     GTGCCCCGGCGGAGGATATATATACCT::CACGTACGCGTACGCGTATATATACGTGCGCTGCTACTCATT
     GCACCTGCTGGGAATT:::::::::::::GTACC::GTACGCGTATATATACGTGCGCTGCTACTCATT
     :::::::::::::::::::::::::::::::::::CGTACGCGTATATATACGTGCGCTGCTACTCATT
     GTGCCCCGGCGGAGGATATATATACCTCACACGTACGCGTACGCGTATATATACGTGCGCTGCTACTCATT
     TACGCACCTGCTGGGAATTGTACCGTACGCGTATATATACGTGCGCTGCTACT Event 10: Callus E7. Clones from LIG3-4 cut fragments
TS   GTGCCCCGGCGGAGGATATATATACCTCACACGTACGCGTACGCGTATATATACGTGCGCTGCTACTCATT
     GTGCCCCGGCGGAGGATATATATACCTCAC::GTACGCGTACGCGTATATATACGTGCGCTGCTACTCATT Event 11: Callus F7. Clones from LIG3-4 cut fragments
TS   GTGCCCCGGCGGAGGATATATATACCTCACACGTACGCGTACGCGTATATATACGTGCGCTGCTACTCATT
     GTGCCCCGGCGGAGGATA:::::::::::::GTACGCGTACGCGTATATATACGTGCGCTGCTACTCATT
     GTGCCCCGGCGGAGGATATATATACCTCAC::GTACGCGTACGCGTATATATACGTGCGCTGCTACTCATT
     GTGCCCCGGCGGAGGATATATATAC:::::::::::::::::::::::GTGCGCTGCTACTCATT Event 12: Callus H5. Clones from LIG3-4 cut fragments
TS   GTGCCCCGGCGGAGGATATATATACCTCACACGTACGCGTACGCGTATATATACGTGCGCTGCTACTCATT
     GTGCCCCG:::::::::::::::::::::::GCGTACGNGTATATATACGTGCGCTGCTACTCATT
     :::::::::::::::::::::::::::::::::::::GCGTATATATACGTGCGCTGCTACTCATT
     GTGCCCCGGCGGAGGATATATATACCTCAC::GTACGCGTACGCGTATATATACGTGCGCTGCTACTCATT
```

B
```
           TACGTGCCCCGGCGGAGGATATATATACCTCACACGTACGCGTACCGCGTATATATACGTGCGCTGCTAC
84634898   TACGTGCCCCGGCGGAGGATATATATACCTCAC::GTACGCGTACGCGTATATATACGTGCGCTGCTAC
84634797   TACGTGCCCCGGCGGAGGATATATATACCTCAC::GTACGCGTACGCGTATATATACGTGCGCTGCTAC
84634907   TACGTGCCCCGGCGGAGGATATATATACCTCAC::GTACGCGTACGCGTATATATACGTGCGCTGCTAC
84634982   TACGTGCCCCGGCGGAGGATATATATACCTCAC::GTACGCGTACGCGTATATATACGTGCGCTGCTAC
84634979   TACGTGCCCCGGCGGAGGATATATATACCTCACA::TACGCGTACGCGTATATATACGTGCGCTGCTAC
84634971   TAC:::::::::::::::::::::::::::::::::::CGTACGCGTATATATACGTGCGCTGCTAC
```

Figure 12

```
12G10   GTGACGCAGATGGATCCAACATTCGAACTAGGGATAACAGGGTAATAATAATAGTAAATGGC
03D07   GTGACGCAGATGGATCCAACATTCGAACTAGGGATAACAGGGTAATAATAATAGTAAATGGC
05H07   GTGACGCAGATGGATCCAACATTCGAACTAGGGATAACAGGGTAATAATAATAGTAAATGGC
03G09   GTGACGCAGATGGATCCAACATTCGAACTAGGGATAA   GGGTAATAATAATAGTAAATGGC
09A05   GTGACGCAGATGGATCCAACATTCGAACTAGGGATAA   GGGTAATAATAATAGTAAATGGC
12C07   GTGACGCAGATGGATCCAACATTCGAACTAGGGATAA   GGGTAATAATAATAGTAAATGGC
04E05   GTGACGCAGATGGATCCAACATTCGAACTAGGGATAA       TAATAATAGTAAATGGC
09G08   GTGACGCAGATGGATCCAACATTCGAACTAGGGATAA          TAATAGTAAATGGC
12F08   GTGACGCAGATGGATCCAACATTCGAACTAGGGATAA          TAATAGTAAATGGC
08G03   GTGACGCAGATGGATCCAACATTCGAACTAGGGATAA
04B12   GTGACGCAGATGGATCCAACATTCGAACTAGGGATA    GGTAATAATAATAGTAAATGGC
01B12   GTGACGCAGATGGATCCAACATTCGAACTAGGGATA    GGGTAATAATAATAGTAAATGGC
01B12   GTGACGCAGATGGATCCAACATTCGAACTAGGGATA    GGGTAATAATAATAGTAAATGGC
09G05   GTGACGCAGATGGATCCAACATTCGAACTAGGGA    ACAGGGTAATAATAATAGTAAATGGC
08H02   GTGACGCAGATGGATCCAACATTCGAACTAGGGA      GGGTAATAATAATAGTAAATGGC
08A09   GTGACGCAGATGGATCCAACATTCGAACTAGGG        GTAATAATAATAGTAAATGGC
01C03   GTGACGCAGATGGATCCAACATTCGAACTA            ATAATAATAGTAAATGGC
10C06   GTGACGCAGATGGATCCAACATTCGAAC        AGGGTAATAATAATAGTAAATGGC
C08     GTGACGCAGATGGATCCAACATTCGAACTAGGGATAA   GGGTAATAATAATAGTAAATGGC
C05     GTGACGCAGATGGATCCAACATTCGAACTAGGGAT     CAGGGTAATAATAATAGTAAATGGC
F11     GTGACGCAGATGGATCCAACATTCGAACTAGGGATA                  GTAAATGGC
C03     GTGACGCAGATGGATCCAACATTCGAACTAGGGA      CAGGGTAATAATAATAGTAAATGGC
E11     GTGACGCAGATGGATCCAACATTCGAACTAGGGA       GGGTAATAATAATAGTAAATGGC
A10     GTGACGCAGATGGATCCAACATTCGAAC         AGGGTAATAATAATAGTAAATGGC
H07     GTGACGCAGATGGATCCAACATTCGAACTAGGGAT
03A08   GTGACGCAGATGGATCCAACATTCGAACTAGGGATAAACAGGGTAATAATAATAGTAAATGGC
12H07   GTGACGCAGATGGATCCAACATTCGAACTAGGGATAAACAGGGTAATAATAATAGTAAATGGC
D02     GTGACGCAGATGGATCCAACATTCGAACTAGGGATAAACAGGGTAATAATAATAGTAAATGGC
11      GTGACGCAGATGGATCCAACATTCGAACTAGGGATAAACAGGGTAATAATAATAGTAAATGGC
H07:    GTGACGCAGATGGATCCAACATTCGAACTAGGGAT::::::::::GACCATGAAGTACGGC
```

METHODS FOR ALTERING THE GENOME OF A MONOCOT PLANT CELL

CROSS-REFERENCE TO RELATED APPLICATIONS

This application claims the benefit of U.S. Patent Application Ser. No. 60/947,003 filed Jun. 29, 2007 and U.S. Patent Application Ser. No. 61/033,150 filed Mar. 3, 2008, which are each herein incorporated by reference in their entirety.

FIELD OF INVENTION

The invention relates to the field of molecular plant biology, in particular, to methods for altering the genome of a monocot plant cell.

BACKGROUND

Recombinant DNA technology has made it possible to insert foreign DNA sequences into the genome of an organism, thus, altering the organism's phenotype. Early on it was recognized that transgenes integrated into a plant genome in a random fashion and in an unpredictable copy number. Thus, efforts were undertaken to control transgene integration in plants.

One method for inserting or modifying a DNA sequence involves introducing a transgenic DNA sequence flanked by sequences homologous to the genomic target and selecting or screening for a successful homologous recombination event. U.S. Pat. No. 5,527,695 issued to Hodges, et al., on Jun. 18, 1996 describes transforming eukaryotic cells with DNA sequences that are targeted to a predetermined sequence of the eukaryote's DNA. Specifically, the use of site-specific recombination is discussed. Transformed cells are identified through use of a selectable marker included part of the introduced DNA sequences.

Other methods relied on homologous recombination-based transgene integration as applied to prokaryotes and lower eukaryotes. With respect to plants, it was shown that artificially induced site-specific genomic double-stranded breaks in plant cells were repaired by homologous recombination with exogenously supplied DNA using two different pathways. (Puchta, et al., (1996) *Proc Natl Acad Sci USA* 93:5055-5060; US Patent Application Publication Number 2005/0172365A1 published Aug. 4, 2005; US Patent Application Publication Number 2006/0282914 published Dec. 14, 2006; WO 2005/028942 published Jun. 2, 2005).

Since the isolation, cloning, transfer and recombination of DNA segments, including coding sequences and non-coding sequences, is most conveniently carried out using restriction endonuclease enzymes. Much research has focused on studying and designing endonucleases such as WO 2004/067736 published Aug. 12, 2004; U.S. Pat. No. 5,792,632 issued to Dujon, et al., Aug. 11, 1998; U.S. Pat. No. 6,610,545 B2 issued to Dujon, et al., Aug. 26, 2003; Chevalier, et al., (2002) *Mol Cell* 10:895-905; Chevalier, et al., (2001) *Nucleic Acids Res* 29:3757-3774; Seligman, et al., (2002) *Nucleic Acids Res* 30:3870-3879.

Although a plethora of approaches have been developed to target a specific site for modification in the genome of a plant, there still remains a need for site-specific modification of a plant genome such that a fertile plant, having the alterated genome, can be recovered.

SUMMARY

The present invention concerns a method to alter a monocot plant cell genome comprising:

(a) contacting at least one monocot plant cell comprising a recognition sequence in its genome with (i) a phenotypic marker, (ii) a DNA fragment, and (ii) a double-strand break inducing agent capable of inducing a double-strand break at the recognition sequence;
(b) selecting cells comprising the phenotypic marker;
(c) identifying cells from step (b) having an alteration in their genome at the recognition sequence wherein the alteration is selected from the group consisting of (i) replacement of at least one nucleotide, (ii) a deletion of at least one nucleotide, (iii) an insertion of at least one nucleotide, and (iv) any combination of (i)-(iii),
wherein identifying comprises any method that does not use a phenotypic marker; and,
(d) recovering a fertile monocot plant having the alteration in its genome.

In a second embodiment, the invention concerns the method of the invention wherein the monocot plant cell is contacted with (i) the phenotypic marker, (ii) the DNA fragment, wherein the DNA fragment comprises a geminiviral origin of replication functional in the monocot plant cell, (iii) a replicase which binds to the geminiviral origin of replication and stimulates replication of the DNA fragment, and (iv) the double-strand break inducing agent capable of inducing a double-strand break at the recognition sequence.

The method of any one of claims 1-2 wherein the alteration at the recognition sequence comprises insertion of a polynucleotide of interest.

In a third embodiment, the DNA fragment in the method of the invention can comprise at least a first region having homology to a genomic region flanking or comprising the recognition sequence.

In a fourth embodiment, the DNA fragment in the method of the invention can comprise in the following order: the first region of homology to the genomic region flanking or comprising the recognition sequence, the polynucleotide of interest, and a second region of homology to the genomic region flanking or comprising the recognition sequence.

In a fifth embodiment of the method of the invention, the alteration at the recognition sequence can comprise replacement, wherein the alteration is produced by homologous recombination.

In a sixth embodiment of the method of the invention, recovery of a fertile monocot plant having the alteration in its genome occurs at a higher frequency as compared to a control method without an inducing agent.

In a seventh embodiment of the method of the invention, identifying in step (c), can comprise at least one method selected from the group consisting of PCR, Southern blot, restriction digest, and DNA sequencing.

In an eighth embodiment of the method of the invention, the DNA fragment comprises a T-DNA.

In a ninth embodiment of the method of the invention, the inducing agent is an endonuclease, a zinc finger nuclease, a transposase, or a site-specific recombinase.

In a tenth embodiment of the method of the invention, the endonuclease is a modified endonuclease that binds an exogenous endonuclease recognition sequence and does not bind an endogenous endonuclease recognition sequence.

BRIEF DESCRIPTION OF THE DRAWINGS

The invention can be more fully understood from the following detailed description and the accompanying drawings and Sequence Listing, which form a part of this application.

FIG. 3. Sequence analysis of modified target sites from PHP27031 events. The I-SceI recognition sequence is shown in regular font. The arrow points to the cleavage site of the upper DNA strand. The 3' overhangs are marked in bold, deleted nucleotides are indicated by colons, and insertions/mutations/deletions are shown in bold grey font. The sequence analysis was performed on DNA extracts from T0 plants (T0s) and then repeated for the T1 generation (T1s). Individual T1 plants are indicated by numbers following the original event annotation (ATST1-250 and ATST1-317).

FIG. 10. Sequence analysis of 12 independent events having modifications of the LIG3-4 endogenous genomic target locus. Panels A and B show alignments of unmodified LIG3-4 sequence (top line each panel) with modified sequences from twelve independent events. DNA was isolated from callus and/or leaf tissue and amplified with LIG3-4 primer pair. The LIG3-4 recognition sequence, or remnants thereof, are shown in bold, the unmodified LIG3-4 sequence is shown in grey text. In some instances the PCR product was directly cloned and sequenced. For other events the PCR product was digested with MluI and products resistant to MluI digestion were cloned and sequenced. In some cases the LIG3-4 PCR product was digested with LIG3-4SC and products resistant to LIG3-4SC digestion were cloned and sequenced.

FIG. 12. LIG3-4SC or MluI enzyme digest of LIG3-4 PCR products from putative events. (A) Agarose gel separation of LIG3-4HD PCR products from PHP34121 T0 plant leaf tissue amplified with LIG3-4 primer pair and then digested with LIG3-4SC nuclease. (B) Sequence analysis and alignment of 6 independent events having modifications of the LIG3-4 endogenous genomic target locus generated by LIG3-4HD. The alignment shows the unmodified LIG3-4 sequence at the top of the panel. The LIG3-4 recognition sequence, or remnants thereof, are shown in bold.

FIG. 16. Sequence analysis of modified target sites in F1 progeny.

Figure 1:
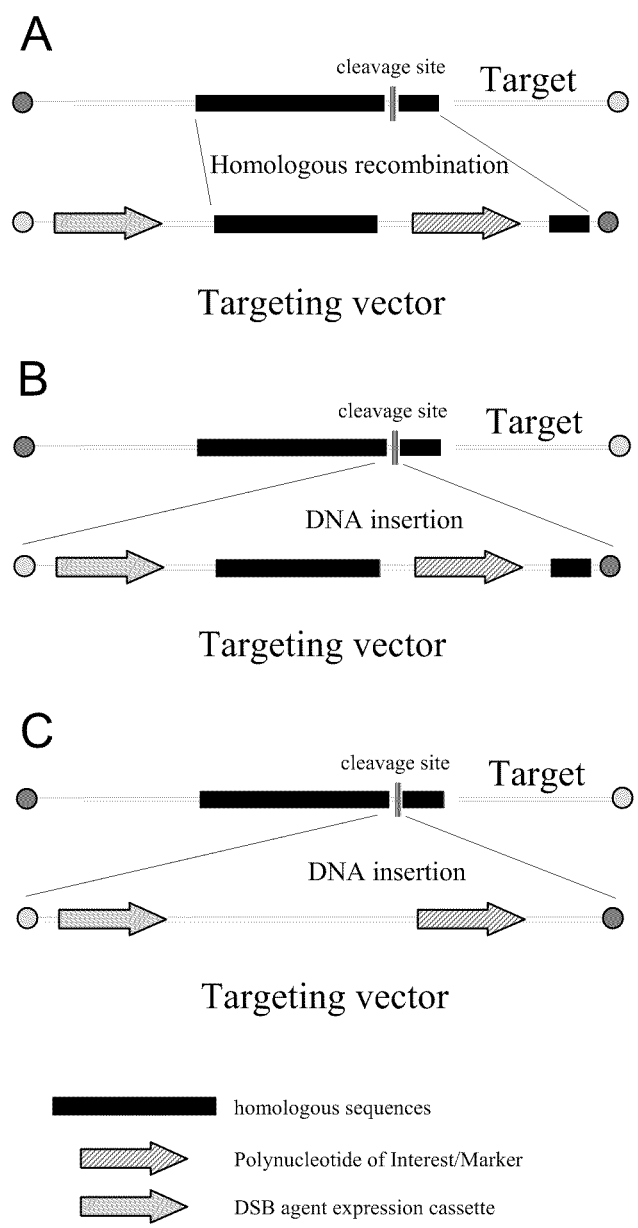
FIG. 1. Several model target sites comprising a double-strand break inducing agent recognition sequence, targeting vector constructs, and possible products are illustrated. (A) represents a generalized vector construct having two regions of homology to the genomic target which flank a polynucleotide of interest and/or marker gene. Homologous recombination will produce an exchange of sequences between the homologous regions at the target site. (B) represents a generalized vector construct having two regions of homology to the genomic target which flank a polynucleotide of interest and/or marker gene. In this example, non-homologous recombination of the DNA fragment will produce an insertion at or near the recognition site. (C) represents a generalized vector construct that does not have regions of homology to the genomic target. Insertion of the DNA fragment will produce an insertion of the polynucleotide of interest at or near the recognition site. In these examples the vectors each comprise an expression cassette for the double-strand break inducing agent. The double-strand break inducing agent can be provided by other constructs or methods.

The Sequence Listing contains one letter codes for nucleotide sequence characters and the single and three letter codes for amino acids as defined in the IUPAC-IUB standards described in *Nucleic Acids Res* 13:3021-3030 (1985) and in the *Biochem J* (1984) 219:345-373.

DETAILED DESCRIPTION

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

In the context of this disclosure, a number of terms and abbreviations are used. The following definitions are provided.

"Open reading frame" is abbreviated ORF.

"American Type Culture Collection" is abbreviated ATCC.

The term "recognition sequence" or "recognition site" as used herein refers to a DNA sequence at which a double-strand break is induced in the plant cell genome by a double-strand break inducing agent. The terms "recognition sequence" and "recognition site" are used interchangeably herein.

The terms "target site", "target sequence", "target locus", "genomic target site", "genomic target sequence", or "genomic target locus" as used interchangeably herein refer to a polynucleotide sequence in the genome of a plant cell that comprises a recognition sequence for a double-strand break inducing agent.

The term "double-strand break inducing agent" as used herein refers to any enzyme which produces a double-strand break at or near the recognition sequence.

As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth, et al., (1984) *Anal Biochem* 138:267-284: $T_m=81.5°$ C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins, et al., (1992) *Comput Appl Biosci* 8:189-191) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins, et al., (1992) *Comput Appl Biosci* 8:189-191) and found in the MegAlign™ v6.1 program of the LASERGENE bioinformatics computing suite (DNASTAR Inc., Madison, Wis.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using a gap creation penalty weight of 50 and a gap length extension penalty weight of 3, and the nwsgap-dna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc Natl Acad Sci USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature, or at a different genetic locas than that found in nature. A "foreign" gene refers to a gene not normally found in the host organism, but that is introduced into the host organism by gene transfer. Foreign genes can comprise native genes inserted into a nonnative organism, or chimeric genes. A "transgene" is a gene that has been introduced into the genome by a transformation procedure.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation recognition sequences, RNA processing sites, effector binding sites, and stem-loop structures.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, N.Y.: Academic Press), pp. 1-82.

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, et al., *Molecular Cloning: A Laboratory Manual*, Cold Spring Harbor Laboratory: Cold Spring Harbor, N.Y. (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for expression of that gene in a foreign host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not all found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones, et al., (1985) *EMBO J* 4:2411-2418; De Almeida, et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, rtPCR, immunoblotting analysis of protein expression, enzyme or activity assays, and/or phenotypic analysis.

The term "expression", as used herein, refers to the production of a functional end-product (e.g., a mRNA or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

As used herein, "transgenic" refers to a plant or a cell which comprises within its genome a heterologous polynucleotide. Typically, the heterologous polynucleotide is stably integrated within the genome such that the polynucleotide is passed on to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollen, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

The present invention concerns a method to alter a monocot plant cell genome comprising:

(a) contacting at least one monocot plant cell comprising a recognition sequence in its genome with (i) a phenotypic marker, (ii) a DNA fragment, and (ii) a double-strand break inducing agent capable of inducing a double-strand break at the recognition sequence;

(b) selecting cells comprising the phenotypic marker;

(c) identifying cells from step (b) having an alteration in their genome at the recognition sequence wherein the alteration is selected from the group consisting of (i) replacement of at least one nucleotide, (ii) a deletion of at least one nucleotide, (iii) an insertion of at least one nucleotide, and (iv) any combination of (i)-(iii), wherein identifying comprises any method that does not use a phenotypic marker; and, (d) recovering a fertile monocot plant having the alteration in its genome.

Any DNA fragment can be used to practice the method of the invention. The DNA fragment can be linear or circular. A DNA fragment is one example of a nucleic acid fragment.

A double-strand break inducing agent is any agent that recognizes and/or binds to a specific polynucleotide recognition sequence to produce a break at or near the recognition sequence. Examples of double-strand break inducing agents include, but are not limited to, endonucleases, site-specific recombinases, transposases, topoisomerases, and zinc finger nucleases, and include modified derivatives, variants, and fragments thereof.

A recognition sequence is any polynucleotide sequence that is specifically recognized and/or bound by a double-strand break inducing agent. The length of the recognition site sequence can vary, and includes, for example, sequences that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

It is possible that the recognition site could be palindromic, that is, the sequence on one strand reads the same in the opposite direction on the complementary strand. The nick/cleavage site could be within the recognition sequence or the nick/cleavage site could be outside of the recognition sequence. In another variation, the cleavage could occur at nucleotide positions immediately opposite each other to produce a blunt end cut or, in other cases, the incisions could be staggered to produce single-stranded overhangs, also called "sticky ends", which can be either 5' overhangs, or 3' overhangs. The recognition sequence can be endogenous or exogenous. When the recognition site is an endogenous sequence, it may be a recognition sequence recognized by a naturally-occurring, or native double-strand break inducing agent. Alternatively, an endogenous recognition site could be recognized and/or bound by a modified or engineered double-strand break inducing agent designed or selected to specifically recognize the endogenous recognition sequence to produce a double-strand break. A modified double-strand break inducing agent can be derived from a native, naturally-occurring double-strand break inducing agent or it could be artificially created or synthesized.

A variety of methods are available to identify those cells having an altered genome at or near the recognition sequence without using a screenable marker phenotype. Such methods can be viewed as directly analyzing a recognition sequence to detect any change in the recognition sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc Natl Acad Sci USA* 82:488-92; Kunkel, et al., (1987) *Meth Enzymol* 154:367-82; U.S. Pat. No. 4,873, 192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff, et al., (1978) Atlas of Protein Sequence and Structure (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double strand break inducing activity are known and generally measure the overall activity and specificity of the agent on DNA substrates containing recognition sites.

Endonucleases are enzymes that cleave the phosphodiester bond within a polynucleotide chain, and include restriction endonucleases that cleave DNA as specific sites without damaging the bases. Restriction endonucleases include Type I, Type II, Type III, and Type IV endonucleases, which further include subtypes. In the Type I and Type III systems, both the methylase and restriction activities are contained in a single complex.

Type I and Type III restriction endonucleases recognize specific recognition sites, but typically cleave at a variable position from the recognition site, which can be hundreds of base pairs away from the recognition site. In Type II systems the restriction activity is independent of any methylase activity, and typically cleavage occurs at specific sites within or near to the recognition site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type its enzymes recognize an asymmetric recognition site and cleave on one side and at a defined distance of about 1-20 nucleotides from the recognition site.

Type IV restriction enzymes target methylated DNA. Restriction enzymes are further described and classified, for example in the REBASE database (webpage at rebase.neb .com; Roberts, et al., (2003) *Nucleic Acids Res* 31:418-20), Roberts, et al., (2003) *Nucleic Acids Res* 31:1805-12, and Belfort, et al., (2002) in *Mobile DNA II*, pp. 761-783, Eds. Craigie, et al., ASM Press, Washington, D.C.

Endonucleases also include meganucleases, which like restriction endonucleases, bind and cut at a specific recognition sequence, however the recognition sites for meganucleases are typically longer, about 18 bp or more. Meganucleases, also known as homing endonucleases (HEases), have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease, meganucleases are also characterized by prefix F—, I—, or PI- for enzymes encoded by free-standing ORFs, introns, and inteins, respectively. For example, intron-, intein-, and freestanding gene encoded meganuclease from *Saccharomyces cerevisiae* are denoted I-SceI, PI-SceI, and F-SceII (HO endonuclease), respectively. Meganuclease domains, structure and function are known, see for example, Guhan and Muniyappa (2003) *Crit Rev Biochem Mol Biol* 38:199-248; Lucas, et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure, et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat, et al., (2003) *Nucleic Acids Res* 31:2952-62; Chevalier, et al., (2002) *Mol Cell* 10:895-905; Gimble, et al., (2003) *Mol Biol* 334:993-1008; Seligman, et al., (2002) *Nucleic Acids Res* 30:3870-9; Sussman, et al., (2004) *J Mol Biol* 342:31-41; Rosen, et al., (2006) Nucleic Acids Res 34:4791-800; Chames, et al., (2005) *Nucleic Acids Res* 33:e178; Smith, et al., (2006) *Nucleic Acids Res* 34:e149; Gruen, et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used as a double-strand break inducing agent including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-Mtul, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any variant or derivative thereof.

The endonuclease can be a modified endonuclease that binds a non-native or exogenous recognition sequence and does not bind a native or endogenous recognition sequence. Modification of the endonuclease can be as little as one nucleotide.

The endonuclease can be provided via a polynucleotide encoding the endonuclease. Such a polynucleotide encoding an endonuclease can be modified to substitute codons having a higher frequency of usage in a plant, as compared to the naturally occurring polynucleotide sequence. For example the polynucleotide encoding the endonuclease can be modified to substitute codons having a higher frequency of usage in a maize plant, as compared to the naturally occurring polynucleotide sequence. In some examples the endonuclease is encoded by SEQ ID NO: 1.

A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity.

One step in the recombination process involves polynucleotide cleavage at or near the recognition site. This cleaving activity can be used to produce a double-strand break. For reviews of site-specific recombinases and their recognition sites, see, Sauer (1994) *Curr Op Biotechnol* 5:521-7; and Sadowski, (1993) *FASEB* 7:760-7. In some examples the recombinase is from the Integrase or Resolvase families.

The Integrase family of recombinases has over one hundred members and includes, for example, FLP, Cre, lambda integrase, and R. The Integrase family has been grouped into two classes based on the structure of the active sites, serine recombinases and tyrosine recombinases. The tyrosine family, which includes Cre, FLP, SSV1, and lambda (λ) integrase, uses the catalytic tyrosine's hydroxyl group for a nucleophilic attack on the phosphodiester bond of the DNA. Typically, members of the tyrosine family initially nick the DNA, which later forms a double strand break. In the serine recombinase family, which includes phiC31 (ΦC31) integrase, a conserved serine residue forms a covalent link to the DNA target site (Grindley, et al., (2006) *Ann Rev Biochem* 16:16). For other members of the Integrase family, see for example, Esposito, et al., (1997) *Nucleic Acids Res* 25:3605-14 and Abremski, et al., (1992) *Protein Eng* 5:87-91.

Other recombination systems include, for example, the streptomycete bacteriophage phiC31 (Kuhstoss, et al., (1991) *J Mol Biol* 20:897-908); the SSV1 site-specific recombination system from *Sulfolobus shibatae* (Maskhelishvili, et al., (1993) *Mol Gen Genet* 237:334-42); and a retroviral integrase-based integration system (Tanaka, et al., (1998) *Gene* 17:67-76).

Sometimes the recombinase is one that does not require cofactors or a supercoiled substrate, including but not limited to Cre, FLP, and active derivatives, variants or fragments thereof. FLP recombinase catalyzes a site-specific reaction during DNA replication and amplification of the two-micron plasmid of *S. cerevisiae*. FLP recombinase catalyzes site-specific recombination between two FRT sites. The FLP protein has been cloned and expressed (Cox, (1993) *Proc Natl Acad Sci USA* 80:4223-7). Functional derivatives, variants, and fragments of FLP are known (Buchholz, et al., (1998) *Nat Biotechnol* 16:617-8, Hartung, et al., (1998) *J Biol Chem* 273:22884-91, Saxena, et al., (1997) *Biochim Biophys Acta* 1340:187-204, and Hartley, et al., (1980) *Nature* 286:860-4).

The bacteriophage recombinase Cre catalyzes site-specific recombination between two lox sites (Guo, et al., (1997) *Nature* 389:40-6; Abremski, et al., (1984) *J Biol Chem* 259: 1509-14; Chen, et al., (1996) *Somat Cell Mol Genet* 22:477-88; Shaikh, et al., (1977) *J Biol Chem* 272:5695-702; and, Buchholz, et al., (1998) *Nat Biotechnol* 16:617-8. Examples of site-specific recombinases that can be used to produce a double-strand break at a recognition sequence, including for example FLP, Cre, SSV1, lambda Int, phi C31, HK022, and R. Examples of site-specific recombination systems used in plants can be found in U.S. Pat. No. 5,929,301; U.S. Pat. No. 6,175,056; WO99/25821; U.S. Pat. No. 6,331,661; WO99/25855; WO99/25841, and WO99/25840, the contents of each are herein incorporated by reference.

Methods for modifying the kinetics, cofactor interaction and requirements, expression, optimal conditions, and/or recognition site specificity, and screening for activity of recombinases and variants are known, see for example Miller, et al., (1980) *Cell* 20:721-9; Lange-Gustafson and Nash, (1984) *J Biol Chem* 259:12724-32; Christ, et al., (1998) *J Mol Biol* 288:825-36; Lorbach, et al., (2000) *J Mol Biol* 296:1175-81; Vergunst, et al., (2000) *Science* 290:979-82; Dorgai, et al., (1995) *J Mol Biol* 252:178-88; Dorgai, et al., (1998) *J Mol Biol* 277:1059-70; Yagu, et al., (1995) *J Mol Biol* 252:163-7; Sclimente, et al., (2001) *Nucleic Acids Res* 29:5044-51; Santoro and Schultze, (2002) *Proc Natl Acad Sci USA* 99:4185-90; Buchholz and Stewart, (2001) *Nat Biotechnol* 19:1047-52; Voziyanov, et al., (2002) *Nucleic Acids Res* 30:1656-63; Voziyanov, et al., (2003) *J Mol Biol* 326:65-76; Klippel, et al., (1988) *EMBO J* 7:3983-9; Arnold, et al., (1999) *EMBO J* 18:1407-14; WO03/08045; WO99/25840; and WO99/25841. The recognition sites range from about 30 nucleotide minimal sites to a few hundred nucleotides.

Any recognition site for a recombinase can be used, including naturally occurring sites, and variants. Variant recognition sites are known, see for example Hoess, et al., (1986) *Nucleic Acids Res* 14:2287-300; Albert, et al., (1995) *Plant J* 7:649-59; Thomson, et al., (2003) *Genesis* 36:162-7; Huang, et al., (1991) *Nucleic Acids Res* 19:443-8; Siebler and Bode, (1997) *Biochemistry* 36:1740-7; Schlake and Bode, (1994) *Biochemistry* 33:12746-51; Thygarajan, et al., (2001) *Mol Cell Biol* 21:3926-34; Umlauf and Cox, (1988) *EMBO J* 7:1845-52; Lee and Saito, (1998) *Gene* 216:55-65; WO01/23545; WO99/25821; WO99/25851; WO01/11058; WO01/07572 and U.S. Pat. No. 5,888,732.

A recombinase can be provided via a polynucleotide that encodes the recombinase or it can be provided via a modified polynucleotide encoding the recombinase. For example, the polynucleotide (encoding a recombinase) can be modified to substitute codons having a higher frequency of usage in a plant, as compared to the naturally occurring polynucleotide sequence or it can be modified to substitute codons having a higher frequency of usage in a maize plant, as compared to the naturally occurring polynucleotide sequence.

Transposases are polypeptides that mediate transposition of a transposon from one location in the genome to another. Transposases typically induce double strand breaks to excise the transposon, recognize subterminal repeats, and bring together the ends of the excised transposon, in some systems other proteins are also required to bring together the ends during transposition.

Examples of transposons and transposases include, but are not limited to, the Ac/Ds, Dt/rdt, Mu–M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta1 elements from *Arabidopsis* (retrotransposon), the P element transposon from *Drosophila* (Gloor, et al., (1991) *Science* 253:1110-1117), the Copia, Mariner and Minos elements from *Drosophila*, the Hermes elements from the housefly, the PiggyBack elements from *Trichplusia ni*, Tc1 elements from *C. elegans*, and IAP elements from mice (retrotransposon). In some examples the transposase is provided via a polynucleotide that encodes the transposase.

It is possible to modify the polynucleotide encoding the transposase by substituting codons having a higher frequency of usage in a plant, as compared to the naturally occurring polynucleotide sequence of by substituting codons having a higher frequency of usage in a maize plant, as compared to the naturally occurring polynucleotide sequence.

DNA topoisomerases modulate DNA secondary and higher order structures and functions related primarily to replication, transcription, recombination and repair. Topoisomerases share two characteristics: (i) the ability to cleave and reseal the phosphodiester backbone of DNA in two successive transesterification reactions; and (ii) once a topoisomerase cleaved DNA intermediate is formed, the enzyme allows the severed DNA ends to come apart, allowing the passage of another single- or double-stranded DNA segment. DNA topoisomerases can be classified into three evolutionary independent families: type IA, type IB and type II.

Those that cleave one strand of DNA and allow single step changes in the linking number of circular DNA are defined as type I DNA topoisomerases. The *Escherichia coli* topoisomerase I and topoisomerase III, *Saccharomyces cerevisiae* topoisomerase III and reverse gyrase belong to the type IA or type I-5' subfamily as the protein link is to a 5' phosphate in the DNA. The prototype of type IB or I-3' enzymes are found in all eukaryotes and also in vaccinia virus topoisomerase I where the protein is attached to a 3' phosphate. Despite differences in mechanism and specificity between the bacterial and eukaryotic enzymes, yeast DNA topoisomerase I can complement a bacterial DNA topoisomerase I mutant (Bjornsti, et al., (1987) Proc Natl Acad Sci USA 84:8971-5). Type IA topoisomerases relax negatively supercoiled DNA and require magnesium and a single-stranded region of DNA. Topoisomerases IB relax both positively and negatively supercoiled DNA with equal efficiency and do not require a single-stranded region of DNA or metal ions for function.

The type II family includes *E. coli* DNA gyrase, *E. Coli* topoisomerase IV (par E), eukaryotic type II topoisomerases, and archaic topoisomerase VI. Type II enzymes are homodimeric (eukaryotic topoisomerase II) or tetrameric (gyrase), cleaving both strands of a duplex. Preferred cutting sites are known for available topoisomerases.

Zinc finger nucleases (ZFNs) are engineered double-strand break inducing agents comprised of a zinc finger DNA binding domain and a double strand break inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. A recognition sequence of 18 nucleotides is long enough to be unique in a mammalian genome ($4^{18}=6.9\times10^{10}$).

To date, designer zinc finger modules predominantly recognize GNN and ANN triplets (Dreier, et al., (2001) *J Biol Chem* 276:29466-78; Dreier, et al., (2000) *J Mol Biol* 303:489-502; Liu, et al., (2002) *J Biol Chem* 277:3850-6), but examples using CNN or TNN triplets are also known (Dreier, et al., (2005) *J Biol Chem* 280:35588-97; Jamieson, et al., (2003) *Nature Rev Drug Discov* 2:361-8). See also, Durai, et al., (2005) *Nucleic Acids Res* 33:5978-90; Segal, (2002) *Methods* 26:76-83; Porteus and Carroll, (2005) *Nat Biotechnol* 23:967-73; zinc-finger consortium (website at www-dot-zincfinger-dot-org); Pabo, et al., (2001) *Ann Rev Biochem* 70:313-40; Wolfe, et al., (2000) *Ann Rev Biophys Biomol Struct* 29:183-212; Segal and Barbas, (2001) *Curr Opin Biotechnol* 12:632-7; Segal, et al., (2003) *Biochemistry* 42:2137-48; Beerli and Barbas, (2002) *Nat Biotechnol* 20:135-41; Carroll, et al., (2006) *Nature Protocols* 1:1329; Ordiz, et al., (2002) *Proc Natl Acad Sci USA* 99:13290-5; Guan, et al., (2002) *Proc Natl Acad Sci USA* 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242.

Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, topoisomerase, or a derivative thereof that retains DNA nicking and/or cleaving activity.

It is possible to provide a zinc-finger nuclease via a polynucleotide that encodes the zinc-finger nuclease. This polynucleotide encoding the zinc-finger nuclease can be modified by substituting codons having a higher frequency of usage in a plant, as compared to the naturally occurring polynucleotide sequence or by substituting codons having a higher frequency of usage in a maize plant, as compared to the naturally occurring polynucleotide sequence.

Sufficient homology or sequence identity indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions (see, for example, Sambrook, et al., (1989) *Molecular Cloning: A Laboratory Manual*, Cold Spring Harbor Laboratory Press, NY; Current Protocols in Molecular Biology, Ausubel, et al., Eds (1994) Current Protocols, a joint venture between Greene Publishing Associates, Inc. and John Wiley & Sons, Inc; and, Tijssen, (1993) *Laboratory Techniques in Biochemistry and Molecular Biology—Hybridization with Nucleic Acid Probes*, Elsevier, N.Y.).

Any means can be used to bring together the various components needed to alter the genome of a monocot plant cell. For example, in in vitro systems, the double strand break inducing agent and the polynucleotide(s) comprising the recognition site(s) can be provided by contacting the components under the appropriate conditions for DNA cleavage.

Alternatively a variety of methods are known for the introduction of nucleotide sequences and polypeptides into an organism, including, for example, transformation, sexual crossing, and the introduction of the polypeptide, DNA, or mRNA into the cell. See, also, WO99/25884.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway, et al., (1986) *Biotechniques* 4:320-34 and U.S. Pat. No. 6,300,543), meristem transformation (U.S. Pat. No. 5,736,369), electroporation (Riggs, et al., (1986) *Proc Natl Acad Sci USA* 83:5602-6, *Agrobacterium*-mediated transformation (U.S. Pat. Nos. 5,563,055 and 5,981,840), direct gene transfer (Paszkowski, et al., (1984) *EMBO J* 3:2717-22), and ballistic particle acceleration (U.S. Pat. Nos. 4,945,050; 5,879,918; 5,886,244; 5,932,782; Tomes, et al., (1995) "Direct DNA Transfer into Intact Plant Cells via Microprojectile Bombardment," in Plant Cell, Tissue, and Organ Culture: Fundamental Methods, ed. Gamborg & Phillips (Springer-Verlag, Berlin); McCabe, et al., (1988) *Biotechnology* 6:923-6; Weissinger, et al., (1988) *Ann Rev Genet* 22:421-77; Sanford, et al., (1987) *Particulate Science and Technology* 5:27-37 (onion); Christou, et al., (1988) *Plant Physiol* 87:671-4 (soybean); Finer and McMullen, (1991) *In Vitro Cell Dev Biol* 27P:175-82 (soybean); Singh, et al., (1998) *Theor Appl Genet* 96:319-24 (soybean); Datta, et al., (1990) *Biotechnology* 8:736-40 (rice); Klein, et al., (1988) *Proc Natl Acad Sci USA* 85:4305-9 (maize); Klein, et al., (1988) *Biotechnology* 6:559-63 (maize); U.S. Pat. Nos. 5,240,855; 5,322,783 and 5,324,646; Klein, et al., (1988) *Plant Physiol* 91:440-4 (maize); Fromm, et al., (1990) *Biotechnology* 8:833-9 (maize); Hooykaas-Van Slogteren, et al., (1984) *Nature* 311:763-4; U.S. Pat. No. 5,736,369 (cereals); Bytebier, et al., (1987) *Proc Natl Acad Sci USA* 84:5345-9 (Liliaceae); De Wet, et al., (1985) in The Experimental Manipulation of Ovule Tissues, ed. Chapman, et al., (Longman, N.Y.), pp. 197-209 (pollen); Kaeppler, et al., (1990) *Plant Cell Rep* 9:415-8) and Kaeppler, et al., (1992) *Theor Appl Genet* 84:560-6 (whisker-mediated transformation); D'Halluin, et al., (1992) *Plant Cell* 4:1495-505 (electroporation); Li, et al., (1993) *Plant Cell Rep* 12:250-5; Christou and Ford (1995) *Annals Botany* 75:407-13 (rice) and Osjoda, et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Useful promoters also encompass promoters utilized for transcription by viral RNA polymerases. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example, Crossway, et al., (1986) *Mol Gen Genet* 202:179-85; Nomura, et al., (1986) *Plant Sci* 44:53-8; Hepler, et al., (1994) *Proc Natl Acad Sci USA* 91:2176-80; and, Hush, et al., (1994) *J Cell Sci* 107:775-84.

For transformation and/or vector construction exemplary, but non-limiting, viral strains and/or genetic elements such as origins or replication, and/or replicases isolated therefrom include, but are not limited to, geminivirus, begomovirus, curtovirus, mastrevirus, (−) strand RNA viruses, (+) strand RNA viruses, potyvirus, potexvirus, tobamovirus, or other DNA viruses, nanoviruses, viroids, and the like, for example, African cassava mosaic virus (ACMV) (Ward, et al., (1988) *EMBO J* 7:899-904; Hayes, et al., (1988) *Nature* 334:179-82), barley stripe mosaic virus (BSM) (Joshi, et al., (1990) *EMBO J* 9:2663-9), cauliflower mosaic virus (CaMV) (Gronenborn, et al., (1981) *Nature* 294:773-6; Brisson, et al., (1984) *Nature* 310:511-4), maize streak virus (MSV) (Lazarowitz, et al., (1989) *EMBO J* 8:1023-32; Shen, et al., (1994) *J Gen Virol* 76:965-9), tobacco mosaic virus (TMV) (Takamatsu, et al., (1987) *EMBO J* 6:307-11; Dawson, et al., (1989) *Virology* 172:285-92), tomato golden mosaic virus (TGMV) (Elmer, et al., (1990) *Nucleic Acids Res* 18:2001-6), and wheat dwarf virus (WDV) (Woolston, et al., (1989) *Nucleic Acids Res* 17:6029-41) and derivatives thereof. See also, Porat, et al., (1996) *Mol Biotechnol* 5:209-21.

Standard DNA isolation, purification, molecular cloning, vector construction, and verification/characterization methods are well established, see, for example Sambrook, et al., (1989) *Molecular Cloning: A Laboratory Manual*, Cold Spring Harbor Laboratory Press, NY. Vectors and constructs include circular plasmids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

Any promoter can be used, and can be selected based on the desired outcome. A promoter is a region of DNA involved in recognition and binding of RNA polymerase and other proteins to initiate transcription. A plant promoter is a promoter capable of initiating transcription in a plant cell, for a review of plant promoters, see, Potenza, et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell, et al., (1985) *Nature* 313:810-2); rice actin (McElroy, et al., (1990) *Plant Cell* 2:163-71); ubiquitin (Christensen, et al., (1989) *Plant Mol Biol* 12:619-32; Christensen, et al., (1992) *Plant Mol Biol* 18:675-89); pEMU (Last, et al., (1991) *Theor Appl Genet* 81:581-8); MAS (Velten, et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1, 3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzenesulfonamide herbicide safeners (De Veylder, et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono, et al., (2004) *Biosci Biotechnol Biochem* 68:803-7) activated by salicylic acid. Other chemical-regulated promoters include steroid-responsive promoters (see, for example, the glucocorticoid-inducible promoter in Schena, et al., (1991) *Proc Natl Acad Sci USA* 88:10421-5; McNellis, et al., (1998) *Plant J* 14:247-257); tetracycline-inducible and tetracycline-repressible promoters (Gatz, et al., (1991) *Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include Kawamata, et al., (1997) *Plant Cell Physiol* 38:792-803; Hansen, et al., (1997) *Mol Gen Genet* 254:337-43; Russell, et al., (1997) *Transgenic Res* 6:157-68; Rinehart, et al., (1996) Plant Physiol 112:1331-41; Van Camp, et al., (1996) *Plant Physiol* 112:525-35; Canevascini, et al., (1996) *Plant Physiol* 112:513-524; Lam, (1994) *Results Probl Cell Differ* 20:181-96; and Guevara-Garcia, et al., (1993) *Plant J* 4:495-505. Leaf-preferred promoters include, for example, Yamamoto, et al., (1997) *Plant J* 12:255-65; Kwon, et al., (1994) *Plant Physiol* 105:357-67; Yamamoto, et al., (1994) *Plant Cell Physiol* 35:773-8; Gotor, et al., (1993) *Plant J* 3:509-18; Orozco, et al., (1993) *Plant Mol Biol* 23:1129-38; Matsuoka, et al., (1993) *Proc Natl Acad Sci USA* 90:9586-90; Simpson, et al., (1958) *EMBO J* 4:2723-9; Timko, et al., (1988) *Nature* 318:57-8. Root-preferred promoters include, for example, Hire, et al., (1992) *Plant Mol Biol* 20:207-18 (soybean root-specific glutamine synthase gene); Miao, et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger, et al., (1990) *Plant Mol Biol* 14:433-43 (root-specific promoter of *A. tumefaciens* mannopine synthase (MAS)); Bogusz, et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri, et al., (1989) *EMBO J* 8:343-50 (Agrobacterium wound-induced TR1' and TR2' genes); VfENOD-GRP3 gene promoter (Kuster, et al., (1995) *Plant Mol Biol* 29:759-72); and rolB promoter (Capana, et al., (1994) *Plant Mol Biol* 25:681-91; phaseolin gene (Murai, et al., (1983) *Science* 23:476-82; Sengopta-Gopalen, et al., (1988) *Proc Natl Acad Sci USA* 82:3320-4). See also, U.S. Pat. Nos. 5,837,876; 5,750,386; 5,633,363; 5,459,252; 5,401, 836; 5,110,732 and 5,023,179.

Seed-preferred promoters include both seed-specific promoters active during seed development, as well as seed-germinating promoters active during seed germination. See, Thompson, et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (see, WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO0/12733, where seed-preferred promoters from end1 and end2 genes are disclosed.

A phenotypic marker is screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See generally, Yarranton, (1992) *Curr Opin Biotech* 3:506-11; Christopherson, et al., (1992) *Proc Natl Acad Sci USA* 89:6314-8; Yao, et al., (1992) *Cell* 71:63-72; Reznikoff, (1992) *Mol Microbiol* 6:2419-22; Barkley, et al., (1980) in *The Operon*, pp. 177-220; Hu, et al., (1987) *Cell* 48:555-66; Brown, et al., (1987) *Cell* 49:603-12; Figge, et al., (1988) *Cell* 52:713-22; Deuschle, et al., (1989) *Proc Natl Acad Sci USA* 86:5400-4; Fuerst, et al., (1989) *Proc Natl Acad Sci USA* 86:2549-53; Deuschle, et al., (1990) *Science* 248:480-3; Gossen, (1993) Ph.D. Thesis, University of Heidelberg; Reines, et al., (1993) *Proc Natl Acad Sci USA* 90:1917-21; Labow, et al., (1990) *Mol Cell Biol* 10:3343-56; Zambretti, et al., (1992) *Proc Natl Acad Sci USA* 89:3952-6; Baim, et al., (1991) *Proc Natl Acad Sci USA* 88:5072-6; Wyborski, et al., (1991) *Nucleic Acids Res* 19:4647-53; Hillen and Wissman, (1989) *Topics Mol Struc Biol* 10:143-62; Degenkolb, et al., (1991) *Antimicrob Agents Chemother* 35:1591-5; Kleinschnidt, et al., (1988) *Biochemistry* 27:1094-104; Bonin, (1993) Ph.D. Thesis, University of Heidelberg; Gossen, et al., (1992) *Proc Natl Acad Sci USA* 89:5547-51; Oliva, et al., (1992) *Antimicrob Agents Chemother* 36:913-9; Hlavka, et al., (1985) Handbook of Experimental Pharmacology, Vol. 78 (Springer-Verlag, Berlin); Gill, et al., (1988) *Nature* 334:721-4.

The cells having the introduced sequence may be grown or regenerated into plants using conventional conditions, see, for example, McCormick, et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including moncot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), pineapple (*Ananas comosus*), banana (*Musa* spp.), palm, ornamentals, and grasses.

The frequency of homologous recombination is influenced by a number of factors. Different organisms vary with respect to the amount of homologous recombination that occurs in their cells and the relative proportion of homologous to non-homologous recombination that occurs is also species-variable. Generally, the length of the region of homology affects the frequency of homologous recombination events, the longer the region of homology, the greater the frequency. The length of the homology region needed to observe homologous recombination is also species-variable. In many cases, at least 5 kb of homology has been utilized, but homologous recombination has been observed with as little as 25-50 bp of homology. The minimum length of homology needed has been estimated at 20-50 bp in *E. coli* (Singer, et al., (1982) *Cell* 31:25-33; Shen and Huang, (1986) *Genetics* 112:441-57; Watt, et al., (1985) *Proc Natl Acad Sci USA* 82:4768-72), 63-89 bp in *S. cerevisaie* (Sugawara and Haber, (1992) *Mol Cell Biol* 12:563-75), and 163-300 bp in mammalian cells (Rubnitz and Subramani, (1984) *Mol Cell Biol* 4:2253-8; Ayares, et al., (1986) *Proc Natl Acad Sci USA* 83:5199-203; Liskay, et al., (1987) *Genetics* 115:161-7).

However, differences in the frequency of homologous recombination can be offset somewhat by sensitive selection for recombinations that do occur. Other factors, such as the degree of homology between the donor and target sequence will also influence the frequency of homologous recombination events. In ES cells, Te Riele, et al., observed that use of targeting constructs based on isogenic DNA resulted in a 20-fold increase in targeting efficiency, and concluded that base sequence divergence between non-isogenic DNA sources was the major influence on homologous recombination efficiency (Te Riele, et al., (1992) *Proc Natl Acad Sci USA* 89:5128-32). Absolute limits for the length of homology or the degree of homology cannot be fixed, but depend on the number of events that can be generated, screened, and selected. All such factors are known and can be taken into account when using the methods and/or compositions for targeted genome modification in any given organism.

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) *Genetics* 147:689-99). Using FLP-mediated DNA integration at a target FRT in *Drosophila*, Golic, et al., showed integration was approximately 10-fold more efficient when the donor and target shared 4.1 kb of homology as compared to 1.1 kb of homology (Golic, et al., (1997) *Nucleic Acids Res* 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) *Proc Natl Acad Sci USA* 90:1262-6; Keeler and Gloor, (1997) *Mol Cell Biol* 17:627-34).

Homologous recombination has also been accomplished in other organisms. For example, at least 150-200 bp of homology was required for homologous recombination in the parasitic protozoan *Leishmania*, regions less than 1 kb a decrease in the length had a linear effect on the targeting frequency, and the targeting frequency plateaus at 1-2 kb of homology (Papadopoulou and Dumas, (1997) *Nucleic Acids Res* 25:4278-86). In the filamentous fungus *Aspergillus nidulans*, gene replacement has been accomplished with as little as 50 bp flanking homology (Chaveroche, et al., (2000) *Nucleic Acids Res* 28:e97). Targeted gene replacement has also been demonstrated in the ciliate Tetrahymena thermophila (Gaertig, et al., (1994) *Nucleic Acids Res* 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically chimeric offspring. By interbreeding siblings, homozygous mice carrying the selected genes can be obtained. An overview of the process is provided in Watson, et al., (1992) *Recombinant DNA*, 2nd Ed., Scientific American Books distributed by WH Freeman & Co.; Capecchi, (1989) *Trends Genet* 5:70-6; and Bronson, (1994) *J Biol Chem* 269:27155-8.

Both homologous recombination and non-homologous recombination occur in mammalian cells. While both processes occur with low frequency, non-homologous recombination occurs more frequently than homologous recombination. Other screening, such as PCR, can also be used to identify desired events. In general, the frequency of homologous recombination is increased as the length of the region of homology in the donor is increased, with at least 5 kb of homology commonly used.

However, homologous recombination has been observed with as little as 25-50 bp of homology. Small deletions or insertions into the target site are introduced with higher frequency than point mutations, but all products can be obtained by appropriate design of donor vector, and selection and/or screening methods. Koller, et al., used a targeting construct to disrupt exon 10 of the CTFR gene in an effort to create a mouse model system for cystic fibrosis (Koller, et al., (1991)

*Proc Natl Acad Sci USA* 88:10730-4). The construct shared homology to 7.8 kb of the target, spanning exon 10, and replaced part of the exon with two neo genes which causes a premature stop codon. A homologous recombination frequency of $4 \times 10^{-4}$ was observed in ES cells. In another example, ES cells comprising two renin genes (Ren-1D and Ren-2) which share about 95% sequence identity at the genomic level, a targeting construct with about 5.5 kb of homology across exons 2-5 of Ren-1D specifically recombined only with the target gene with a homologous recombination frequency of $5.29 \times 10^{-3}$ (Miller, et al., (1992) *Proc Natl Acad Sci USA* 89:5020-4). It was estimated that the frequency observed was enhanced about 2.7-fold by the inclusion of a negative selectable marker in the targeting construct.

In order to study the transcriptional control of type I collagen, the first intron of ColIA1 was targeted in mouse ES cells (Hormuzdi, et al., (1998) *Mol Cell Biol* 18:3368-75). The targeting construct, which shared about 13 kb of homology to the target, resulted in a 1.3 kb deletion in intron 1. Even though there is a large deletion in the first intron, the study showed the intron was still correctly spliced. A point mutation in β-globin causes sickle cell disease. Using a mouse-human hybrid cell line, BSM, which contains human chromosome 11, the sickle cell allele βS-globin was corrected to the normal βA-globin allele (Shesley, et al., (1991) *Proc Natl Acad Sci USA* 88:4294-8). The targeting vector comprised 4.7 kb of homology to the β-globin gene, as well as a selectable marker outside of the target gene, and resulted in a homologous recombination frequency of at least $1 \times 10^{-4}$. Homologous recombination in mammals other than mouse has been limited by the lack of stem cells capable of being transplanted to oocytes or developing embryos. However, McCreath, et al., (*Nature* 405:1066-9 (2000)) reported successful homologous recombination in sheep by transformation and selection in primary embryo fibroblast cells. The targeted fibroblast nuclei were transferred to enucleated egg cells followed by implantation in the uterus of a host mother to produce a homozygous, non-chimeric offspring, however the time available for targeting and selection is short.

Error-prone DNA repair mechanisms can produce mutations at double-strand break sites. The nonhomologous end-joining (NHEJ) pathways are the most common repair mechanism to bring the broken ends together (Bleuyard, et al., (2006) *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik, et al., (2000) *EMBO J* 19:5562-6), however if two different double-strand breaks occur, the free ends from different breaks can be ligated and result in chromosomal deletions (Siebert and Puchta, (2002) *Plant Cell* 14:1121-31), or chromosomal translocations between different chromosomes (Pacher, et al., (2007) *Genetics* 175:21-9).

Episomal DNA molecules can also be ligated into the double-strand break, for example, integration of T-DNAs into chromosomal double-strand breaks (Chilton and Que, (2003) *Plant Physiol* 133:956-65; Salomon and Puchta, (1998) *EMBO J* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (S, G2, M phases of a cell cycle) (Molinier, et al., (2004) *Plant Cell* 16:342-52). Ectopic and/or epigenic DNA sequences may also serve as a DNA repair template for homologous recombination (Puchta, (1999) *Genetics* 152:1173-81).

The formation of a synaptic complex of recombinase monomers with two target sites is not required for the initial nicking of the target site DNA (Prado, et al., (2000) *Mol Gen Genet.* 263:73-80). The nicked sites are likely prone to DNA repairs that may lead to their modification and inactivation. Double-strand breaks can be formed when replication forks face a nick at the replicating template DNA strand (Cortes-Ledesma and Aguilera (2006) *EMBO Rep* 7:919-26; Kuzminov, (2001) *Proc Natl Acad Sci USA* 98:8241-6). These are frequently repaired by non-homologous end joining leading to mutations.

Members of the serine family of recombinases produce double-strand breaks at the recombination sites as a part of their catalytic activities (Grindley, et al., (2006) *Ann Rev Biochem* 16:16). The R/RS system in sweet orange appeared to induce mutations of RS sites leading to chromosomal deletions not associated with site-specific recombination reactions per se (Ballester, et al., (2006) *Plant Cell Rep* 26:39-45).

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter, et al., (1992) *Mol Gen Genet* 231:186-93; Offringa, et al., (1990) *EMBO J* 9:3077-84; Offringa, et al., (1993) *Proc Natl Acad Sci USA* 90:7346-50; Paszkowski, et al., (1988) *EMBO J* 7:4021-6; Hourda and Paszkowski, (1994) *Mol Gen Genet* 243:106-11; and Risseeuw, et al., (1995) *Plant J* 7:109-19.

An endogenous, non-selectable gene was targeted in *Arabidopsis* using a targeting vector containing a region of about 7 kb homologous to the target gene and the targeting frequency was estimated to be at least 3.9×10−4 (Maio and Lam, (1995) *Plant J* 7:359-65). In another example, using a positive-negative selection scheme and a targeting vector containing up to 22.9 kb of sequence homologous to the target, Thykjæer and co-workers detected homologous recombination with a frequency less than $5.3 \times 10^{-5}$, despite the large flanking sequences available for recombination (Thykjæer, et al., (1997) *Plant Mol Biol* 35:523-30). In *Arabidopsis*, the AGL5 MADS-box gene was knocked out by homologous recombination using a targeting construct consisting of a kanamycin-resistance cassette inserted into the AGL5 sequence roughly 3 kb from the 5' end and 2 kb from the 3' end. Of the 750 kanamycin-resistant transgenic lines that were generated, one line contained the anticipated insertion (Kempin, et al., (1997) *Nature* 389:802-3). Hanin, et al., obtained homologous recombination events at a basal frequency of $7 \times 10^{-4}$ using 3 kb 5'-end and 2 kb 3'-end homology to the *Arabidopsis* PPO gene encoding protoporphyrinogen oxidase (Hanin, et al., (2001) *Plant J* 28:671-7). Terada, et al., targeted the Waxy locus in rice using an *Agrobacterium*-mediated transformation procedure. Negative selection, in form of two copies of the diphteria toxin gene placed at both ends of T-DNA, was used to eliminate random integration of T-DNAs, allowing for enrichment of rare homologous recombination events in the selected material, and their transformation system generated thousands of events from just 150 rice seeds. The reported frequency of homologous recombination of the waxy gene in rice was $0.65 \times 10^{-3}$, without inclusion of elements to enhance homologous recombination (Terada, et al., (2002) *Nat Biotech* 20:1030-4).

DNA double-strand breaks (DSBs) appear to be an effective factor to stimulate HR pathways in every organism tested to date (Puchta, et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, two- to nine-fold increase of homologous recombination was observed between artificially constructed homologous DNA repeats in plants (Puchta, et al., (1995) *Plant Mol Biol* 28:281-92). In maize protoplasts, experiments with linearized DNA molecules demonstrated enhanced homologous recombination between plasmids (Lyznik, et al., (1991) *Mol Gen Genet* 230:209-18).

The effects of DSBs on homologous recombination have been investigated by using rare-cutting enzymes such as HO and I-SceI as well as transposons such as Ac and Mutator (Chiurazzi, et al., (1996) *Plant Cell* 8:2057-66; Puchta, et al., (1996) *Proc Natl Acad Sci USA* 93:5055-60; Xiao and Peterson, (2000) *Mol Gen Genet* 263:22-9; and Shalev and Levy (1997) *Genetics* 146:1143-51). Chiurazzi, et al., ((1996) *Plant Cell* 8:2057-66) introduced DSBs into an *Arabidopsis* chromosome using HO-endonuclease and observed 10-fold increase in the frequency of homologous recombination between repeats flanking the HO recognition site. Excision of Ac transposable elements also stimulated homologous recombination between repeats flanking the elements at an even higher frequency (Xiao and Peterson (2000) *Mol Gen Genet* 263:22-9).

Puchta, et al., reported that homologous recombination frequency at an artificial target locus was increased by up to two orders of magnitude when DSBs were generated using I-SceI (Puchta, et al., (1996) *Proc Natl Acad Sci USA* 93:5055-60). In this experiment, I-SceI expression cassette was introduced into transgenic tobacco target lines together with targeting construct by co-inoculation with the two respective *Agrobacterium* strains. Homologous recombination between T-DNA containing the targeting construct and the target site reconstituted the kanamycin-resistance gene (nptII). There was an apparent correlation between frequency of homologous recombination and the amount of I-SceI expression cassette, suggesting that more DSBs yielded higher HR frequency.

Recently, Wright, et al., reported high frequency of homologous recombination at an artificial target site pre-introduced into tobacco plants using a zinc-finger nuclease (ZFN) (Wright, et al., (2005) *Plant J* 44:693-705). The zinc-finger nuclease expression cassette and targeting vectors were introduced into protoplasts by co-electroporation and homologous recombination was monitored by kanamycin resistance and GUS activity. In approximately every 10 transformants, one event was observed in which targeted modification occurred, however, only 20% of the modified events contained the desired homologous recombination products as indicated by Southern blot analysis. While Terada, et al., (2002) recovered targeted events by producing a massive number of transgenic events, the experimental designs utilizing double-strand break technologies demonstrate the promises of these methods (Terada, et al., (2002) *Nat Biotech* 20:1030-4). Experiments in mammalian cells indicated that numerous breaks induced by restriction endonucleases resulted in a decrease in homologous recombination, however different enzymes showed different repair patterns and frequencies within the study and as compared to studies in other organisms (Manivasakam, et al., (2001) *Nucleic Acids Res* 29:4826-33).

Zinc finger nucleases are engineered endonucleases with altered specificities, for example by fusion of an engineered DNA binding domain to an endonuclease, for example, FokI (Durai, et al., (2005) *Nucleic Acids Res* 33:5978-90; Mani, et al., (2005) *Biochem Biophys Res Comm* 335:447-57). Wright, et al., (2005) and Lloyd, et al., (2005) reported a high frequency mutagenesis at a DNA target site integrated into tobacco or *Arabidopsis* chromosomal DNA using zinc-finger nucleases (Wright, et al., (2005) *Plant J* 44:693-705; Lloyd, et al., (2005) *Proc Natl Acad Sci USA* 102:2232-7). In human cells, the application of zinc finger nucleases has successfully targeted the IL2Rγ gene endogenous locus (Urnov, et al., (2005) *Nature* 435:646-51).

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould, et al., (2006) *J Mol Biol* 355:443-58; Ashworth, et al., (2006) *Nature* 441:656-9; Doyon, et al., (2006) *J Am Chem Soc* 128:2477-84; Rosen, et al., (2006) *Nucleic Acids Res* 34:4791-800; and Smith, et al., (2006) *Nucleic Acids Res* 34:e149). Engineered meganucleases have been demonstrated that can cleave cognate mutant sites without broadening their specificity.

EXPERIMENTAL

The following examples are offered by way of illustration and not by way of limitation. The present invention is further defined in the following Examples, in which parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "seq" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

As is discussed in the Examples below, it was observed during evaluation of I-SceI meganuclease, that maize optimized I-SceI (SEQ ID NO: 1) efficiently generated DNA double-strand breaks in maize. By detecting changes to, or loss of the artificial target site (ATS2), about 80% of the target sites sustained DNA double-strand breaks (0.8 mutations per allele). Most DSBs were repaired by non-homologous end-joining. All types of mutations, including deletions (1 to 500 bp), insertions, and substitutions were observed at the specific target sites. A similar rate of site-directed mutagenesis is expected at any gene in the corn genome using any double-strand break inducing agent specific to a target sequence. Using a simple screening procedure described herein, it is practical to obtain desired site-directed mutagenesis on any given gene. I-SceI is a site-specific homing endonuclease encoded by a mitochondrial intron of *Saccharomyces cerevisiae*. It recognizes and cleaves an intronless allele of their cognate gene to insert a copy of the intron by a double-strand break repair mechanism. The I-SceI protein binds and cleaves an 18 bp long recognition sequence (SEQ ID NO: 2):

```
5'-T A G G G A T A A^C A G G G T A A T-3'
3'-A T C C C^T A T T G T C C C A T T A-5'
```

Using double-strand breaks introduced by I-SceI, the DNA repair products were analyzed in transgenic maize plants. No selection for the repair products was applied after re-transformation of the I-SceI target-containing cells with the I-SceI expression vector. Instead, the T0 re-transformed plants were screened by PCR to identify modifications of the I-SceI recognition site. Within a pool of T0 plants containing the PCR-amplifiable target locus, about 60-80% showed short deletions and insertions around the I-SceI restriction site, which were similar in structure to I-SceI induced mutations in other plant species. Eight putative homologous recombination events were identified among 1380 T0 plants screened by PCR, three of these eight events which were sequenced and confirmed that the modified target site comprised a precise insertion of the T-DNA fragment flanked by homologous regions. In about 1% of analyzed samples T-DNA integrations into the I-SceI target site were observed.

The PCR screen was designed to identify the T-DNA left border ligated at the right end of the I-SceI-induced double-strand break. While short deletions and insertions were observed at these junction sites, the T-DNA right border frequently integrated into double-strand break without modifications. Other large rearrangements, which resulted in the target site not being capable of amplification by PCR, were observed indicating that expression of I-SceI frequently destabilized the target locus. In maize, sequence analysis showed DNA repair took place at or toward the 3' end of the I-SceI restriction site, and we observed very minor modifications in the target site such as one base deletion. Such events were not reported in *Arabidopsis* and tobacco, likely due to selection scheme(s) that would not detect any minor modifications. These experiments demonstrate that maize is amenable to site specific modification of its genome using double-strand breaks to produce sequence modifications including mutations, gene knockouts, site-specific integration, and homologous recombination events. The experimental system was designed for recovery of mutations, T-DNA insertions, and homologous recombination products at the I-SceI target site, with no selection for any particular DNA repair products. Since the DNA repair mechanisms vary between different plant species (Kirik, et al., (2000) *EMBO J* 10:5562-6; Orel and Puchta, (2003) *Plant Mol Biol* 51:523-31), the DNA repair substrates, products, and putative stimulatory cofactors had to be evaluated and confirmed in maize.

The strategies employed to enhance the frequency of genomic alterations do not rely on the re-assembly of a functional marker, coding region, or expression cassette via homologous recombination or targeted insertion at the recognition site. The identification of the plant cells produced by the methods having genomic alteration(s) of the recognition sequence was not prejudiced by any particular expectation or selection for a specific product. Consequently all possible products, including sequence alterations, DNA insertions, and homologous recombinations, were generated, observed, and directly identified using the same experimental compositions and methodology as described below. One of skill in the art would recognize alternative compositions and methods which fall within the scope of this teaching, but which are not necessarily explicitly outlined herein.

Example 1

Maize lines comprising an introduced I-SceI recognition sequence flanking by regions of homology (ATS2) were produced as described in Example 4. Immature embryos comprising ATS2 were used for retransformation with the vectors described below.

A. PHP22066

A control vector that does not contain either the moI-SceI coding region or homology regions was constructed using standard molecular biology techniques. PHP22066 comprises the following operably linked components:

Ubi pro::ubi 5' UTR::GAT4621::pinII wherein ubi pro is the maize ubiquitin promoter, ubi 5' UTR is the 5' untranslated region of the maize ubiquitin gene, GAT4621 encodes a glyphosate acetyltransferase, and pinII is the transcription termination sequence from potato proteinase inhibitor II.

Maize immature embryos 9-12 days after pollination (DAP) hemizygous for ATS2 were re-transformed with control vector PHP22066 using *Agrobacterium*-mediated methods essentially as described in Example 2B1.

Figure 2:
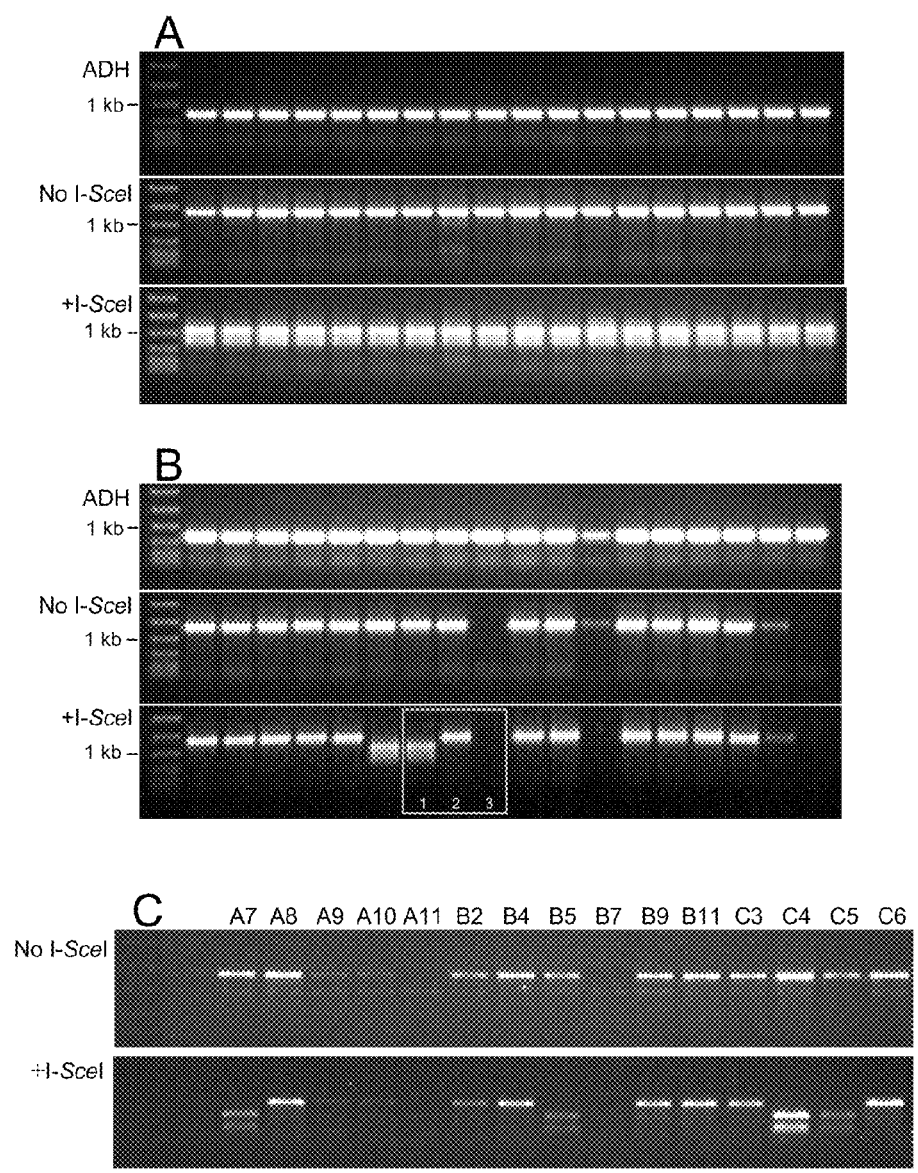
FIG. 2. PCR-based screen and sequence analysis of modified target sites. PCR amplified fragments from events containing the I-SceI restriction site were run on agarose gels before and after digestion with I-SceI endonuclease (−I-SceI and +I-SceI, respectively). Intact I-SceI sites should produce two fragments, while modified sites should make the fragments refractory to digestion. (A) Events from PHP22066 which has no I-SceI expression cassette. (B) Events from PHP30662 which has an I-SceI expression cassette, but no homology regions to ATS2. (C) Events from PHP27031 which has an I-SceI expression cassette and two homology regions to ATS2 (re-transformation events A7 through C6).

Successful delivery of the vector confers glyphosate resistance, and was used to identify putative events by callus selection on media containing 1 mM glyphosate. Plants regenerated from stable transformants using standard culture and regeneration conditions were screened for modification(s) of ATS2 as described in Example 5. No evidence of double-strand breaks was found for any events generated from control vector PHP22066 using the same PCR and other screening techniques described for experiments using I-SceI expression vectors as described below (see, FIG. 2A).

B. I-SceI Expression Vectors

Vectors comprising a maize codon-modified I-SceI (moI-SceI) double-strand break (dsb) inducing agent expression cassette were generated using standard molecular biology techniques for delivery into maize embryos. The strategies employed for generating and selecting genomic alterations produced do not employ reconstitution of a selectable marker expression cassette, therefore the dsb inducing agent vectors do not have a fragment of a selectable marker cassette. In this example, the dsb inducing agent vectors do have a phenotypic marker expression cassette encoding GAT4621, which is used to validate successful delivery of the vector.

1. PHP30662

A vector comprising an I-SceI expression cassette and GAT4621 positive marker gene was constructed without regions of homology to ATS2. TV-PHP30662 comprises the following operably linked components:

Ubi pro::ubi 5' UTR::moI-SceI::pinII-ubi pro::ubi 5' UTR::GAT4621::pinII

Maize 9-12 DAP immature embryos hemizygous for ATS2 line were re-transformed with moI-SceI expression vector PHP30662 using *Agrobacterium*-mediated methods essentially as described in Example 2B1.

Successful delivery of the vector confers glyphosate resistance, and was used to identify putative events by callus selection on media containing 1 mM glyphosate. Plants regenerated from stable transformants using standard culture and regeneration conditions were screened for modification(s) of ATS2 as described in Example 5. Re-transformation of ATS2 embryos with the moI-SceI expression vector PHP30662 produced sequence modifications at the I-SceI recognition site of ATS2 indicative of repair of double-strand breaks as evidenced by PCR screening for the ATS2 site. Double-strand break event identification protocol did not rely on activation/inactivation of moPAT::YFP; instead, all glyphosate-resistant events were screened by PCR assays and/or Southerns and/or sequencing as described in Example 5 to identify and characterize events and modifications generated. Consistently, in three experiments, about 10% of selected PHP30662 events (5/52, 23/253, and 16/161) did not contain a PCR-amplifiable ATS2 site (ATS2 null), indicative of a possible DNA insertion, or large deletion, at or near the double-strand break. A summary of separate re-transformation experiments is provided in TABLE 1.

TABLE 1

| Vector | # plants analyzed | # ATS2 modified site | # ATS2 null events | # ATS2 null plants |
|---|---|---|---|---|
| PHP22066 | 50 | 0 | 0 | — |
| PHP30662 | 52 | 37 | 5 | — |
|  | 253 | — | 23 | 31 |
|  | 161 | — | 16 | 22 |

Overall 836 glyphosate resistant plants were generated and at least partially characterized. From these about 80% of glyphosate resistant events from PHP30662 showed evidence of some DNA rearrangement near the ATS2 site by PCR, indicating that regions of homology do not significantly affect the frequency of double-strand break induction and/or repair at the ATS2 site. The ATS2 site is amplified using primers to moPAT and YFP regions. From 836 analyzed plants, 92 plants are ATS2 null by PCR. From these 92 ATS2 null plants, about 46% (42/92) retained the YFP coding region as determined by PCR for YFP, however only about 9% (8/92) of these ATS2 null events retained the moPAT coding region as determined by PCR for moPAT. It was expected that a T-DNA insertion at the double-strand break without other major rearrangements would be ATS2 null by PCR, YFP+ and moPAT+ by PCR. Four putative insertion events were identified by PCR, one event (75786272) has been confirmed by sequencing to be a T-DNA insertion at the I-SceI recognition site. A summary of events and characterization is presented in TABLE 2.

TABLE 2

| Vector | #embryos | Total events | Total plants | # plants analyzed | ATS2 null plants | ATS2 null YFP+ | ATS2 null PAT+ | YFP+ PAT+ |
|---|---|---|---|---|---|---|---|---|
| 22066 | 550 | 116 | 229 | 123 | 0 | 0 | — | — |
| 30662 | 5346 | 609 | 1155 | 836 | 92 | 42 | 8 | 4 |

2. PHP27031

A vector comprising the I-SceI expression cassette derived from PHP22603, and GAT4621 positive selectable marker gene, flanked by two DNA segments homologous to the ATS2 target site were constructed. The homologous segments are a 3019 bp HR1 segment containing YFP coding region and *Arabidopsis* gAt; and a 924 bp HR2 segment containing moPAT. The GAT4621 gene was asymmetrically positioned within the homology region to facilitate the identification of homologous recombinants by PCR. Vector TV-ATS2 PHP27031 comprises the following operably linked components:

Ubi pro::ubi 5' UTR::moI-SceI::pinII-HR1-ubi pro::ubi 5' UTR::GAT4621::pinII-HR2

Maize 9-12 DAP immature embryos from ATS2 line(s) were re-transformed with the PHP27031 moI-SceI expression vector using *Agrobacterium*-mediated methods essentially as described in Example 2B1. Re-transformation of ATS2 embryos with the moI-SceI expression cassette produced double-strand breaks at the I-SceI recognition site of ATS2. Successful delivery of PHP27031 confers glyphosate resistance, which was used to identify putative PHP27031 events by callus selection on media containing 1 mM glyphosate. The event identification protocol did not rely on activation/inactivation of moPAT::YFP; instead, all glyphosate-resistant events were screened by PCR assays and/or Southerns for modifications of ATS2 without presupposing the type of modification produced. About 80% of glyphosate resistant material showed evidence of some DNA rearrangement, indicating that double-strand breaks may be used for directed mutagenesis of chromosomal DNA, for example, to knockout expression of selected genes.

In preliminary experiments there were indications that some selected calli and T0 plants regenerated therefrom contained different alterations of the ATS2 site. For successful isolation of a particular event, samples for the PCR screening were taken from the population of T0 regenerated plants regardless whether they were originating from the same or different selected calli. No more than five T0 plants were routinely obtained from a single selected callus. In subsequent experiments, typically only one event was propagated from each embryo/callus.

A large-scale re-transformation experiment was done using PHP27031 introduced into transgenic embryos hemizygous for ATS2 and putative events were identified by resistance to glyphosate. These events were further screened and characterized by PCR for presence and/or change in ATS2 (FIGS. 3A, 3C), sensitivity to I-SceI endonuclease digestion (FIG. 2A), presence of T-DNA border sequences (FIGS. 3B, 3C), presence of homologous regions (FIG. 3C, FIG. 6), GAT coding region (FIG. 3C) (see, Example 5A); Southern blots were performed using probes for YFP (FIGS. 4A, 4B) (see, Example 5B); and sequence analysis of ATS2 and junctions (FIG. 1, FIG. 5) (see, Example 5C). In one round of transformation experiments 6339 hemizygous embryos from ATS2 line 2248 were retransformed with PHP27031, 1033 glyphosate resistant calli were recovered, and 1380 plants propagated from those calli. Selected plants were partially or fully screened and/or characterized as described in Example 5.

3. PHP 28040

A modified version of the basic targeting vector comprising an I-SceI expression cassette was constructed. The vector comprises the I-SceI expression cassette, the wheat dwarf virus (WDV) short intergenic region (SIR), replicase (Rep), and origin of replication (LIR), and GAT4621 positive marker expression cassette flanked by two DNA segments homologous to the ATS2 target site (HR1 and HR2) was constructed. Two wildtype FLP recombination targets (FRT) were added to optionally excise random integrations of the targeting vector into the genome, using the FLP expression cassette in ATS2 (PHP22709).

Replicating DNAs are expected to persist longer in the transformed cells, providing more substrate and time for DNA recombination, including homologous recombination. Replication activity was provided by the wheat dwarf virus replication-associated protein (Rep) with its cognate origin of replication (LIR). We used a modified version of Rep that did not contain intron sequences between two open reading frames RepA and RepB to produce a longer transcript encompassing both reading frames (RepAB). We tested RepAB and confirmed replication activity in BMS cells (data not shown). It is possible that strong expression of RepAB may negatively impact growth of transformed tissues. If this is the case, the Rep cassette may also act as a form of negative selection against random integrations, thus helping to identify potential target modification events. PHP28040 comprises the following operably linked components:

FRT-Ubi pro::ubi 5' UTR::moI-SceI::pinII-WDV SIR::WDV RepAB::WDV LIR-HR1-ubi pro::ubi 5' UTR::GAT4621::pinII-HR2-FRT One thousand two hundred forty two maize 9-12 DAP immature embryos hemizygous for the ATS2 locus were re-transformed with the moI-SceI expression vector PHP28040 using *Agrobacterium*-mediated methods essentially as described in Example 2B1.

Successful delivery of the vector confers glyphosate resistance, and is used to identify putative events by callus selection on media containing 1 mM glyphosate. Re-transformation of ATS2 embryos with the moI-SceI expression vector PHP28040 is expected to produce sequence modifications at the I-SceI recognition site of ATS2 indicative of repair of double-strand breaks identified by PCR screening for the ATS2 site. The event identification protocol does not rely on activation/inactivation of a marker, for example, moPAT:: YFP. Instead, all glyphosate-resistant events are screened by PCR assays and/or Southerns and/or sequencing as described in Example 5 to identify and characterize events and modifications generated.

It is expected that PHP28040 will induce modification of ATS2 at a frequency equivalent to or greater than the average frequency (~80%) observed for PHP27031 or PHP33062. The frequency ATS2 null events is also expected to be equivalent or greater than the average frequency observed for PHP27031 or PHP33062 of 8-10%. The ATS2 null events include DNA insertions at ATS2, or large deletions of sequence. The frequency of homologous recombination events is expected to be enhanced by the addition of the replication function as compared to the frequency observed for PHP27031. In addition, it is expected that fewer random transgenic events will be produced as a result of negative selection for random insertions of T-DNA, therefore fewer events will have to be analyzed in order to identify gene targeting events.

4. PHP 28184

Another modified version of the basic targeting vector comprising an I-SceI expression cassette was constructed in order to provide the nuclease using a crossing strategy described in Example 7. The vector comprises a replicon comprising I-SceI nuclease and WDV replicase (Rep) under control of the WDV bidirectional promoter (LIR) comprising the origin of replication flanked by wild type FRT sites. The vector also comprises a BAR positive marker expression cassette. The FLP recombinase is provided by the ATS2 lines generated by transformation with PHP22709. Crossing donor plants to ATS2 target plants results in excision and activation of the I-SceI replicon. Results of crossing experiments using PHP28184 are discussed below in Example 7.

PHP28184 comprises the following operably linked components:
35S pro::BAR::pinII-FRT-LIR::moI-SceI::pinII-moPAT::YFP-pinII::WDV Rep-FRT Maize plants comprising the I-SceI replicon were generated by transforming maize immature embryos with vector PHP28184 essentially as described in Example 2B1. Target vector donor events were selected for Bialaphos resistance and plants regenerated using standard media and methods.

Results

The majority, approximately 80%, of glyphosate-resistant plants from PHP30662 or PHP27031 acquired some sequence alteration and/or insertion at the I-SceI restriction site. A random sample of 15 T0 events from PHP27031 was assayed by PCR for I-SceI restriction site integrity (FIG. 2A). PCR was used to amplify a 1606 bp fragment containing the I-SceI site (panel–I-SceI), these PCR products were digested with I-SceI endonuclease and run on a gel (panel+I-SceI). Among eleven samples that produced strong PCR signal, seven amplification products were not cut by I-SceI indicating mutations of the target site. FIG. 3B illustrates mutations found at the I-SceI site in a sample of sequenced events from two rounds of re-transformation experiments. These modifications were centered around the I-SceI site, suggesting that DNA restriction by I-SceI was a primary cause of these mutations. Among other alterations of the I-SceI site, a single nucleotide deletion and two nucleotide deletion were responsible for the inactivation of the I-SceI sites in the B9 and C6 events, respectively (FIG. 3B). Two other alterations, events 250 and 317, were selected and characterized in the next generation, the alterations observed in the T0 generation were stably maintained in the individual progeny of T1s (FIG. 2B). Mutations at the I-SceI site occurred in about 80% of T0 plants in various experimental runs, which corresponds well with the larger sample of tested events from the preliminary re-transformation experiments.

Selected glyphosate-resistant T0 plants were screened for structural integrity of the ATS2 site using a pair of primers specific to the DNA regions flanking the I-SceI restriction site. The ATS PCR reaction produces a 1138 bp fragment from the intact ATS2 site. About 20% of pre-screened PHP27031 DNA samples (126 out of 645) did not produce the amplification product (FIG. 3A). These samples were advanced for further analysis. Although PCR-negative events were selected, the pre-screening procedure was also a positive selection for apparently intact ATS2 events, which may comprise small sequence alterations that do not affect PCR amplification and/or band size. Two additional PCR screens were designed to amplify potential junction sites between the T-DNA left border and the left side of the I-SceI double-strand break (T-DNA LB), and the junction sites within the short homologous region between T-DNA and ATS (FIG. 3C, panel HR). The PCR-positive signal from the LB PCR screen identifies potential T-DNA insertion events. The PCR-positive signal from the HR screen identifies potential homologous recombination events.

All pre-selected PHP27031 events were subsequently re-evaluated by a second round of PCR reactions using new, higher quality DNA preparations (FIG. 3C). From a sample of the pre-screened events shown in FIG. 3C, all events selected from plate #6 did not amplify ATS2 site and the 6C3 event showed relatively strong amplification signal for the T-DNA left border junction site. The same signal from the 7G8 event was coexisting with the ATS2 amplification product (FIG. 3C, panel T-DNA LB). The 8B2 event showed a clear signal of a potential homologous recombination product (FIG. 3C, panel HR). Events 7A5 and 9A5 apparently escaped the pre-screening procedure, while event 7G10 contained a shortened ATS2 compared to the original ATS2 target site (FIG. 3C, panel ATS). Based on PCR-screening results, 53 T0 plants were moved to the greenhouse and thirty-six of them were used for additional DNA extractions and analyses.

Figure 4:
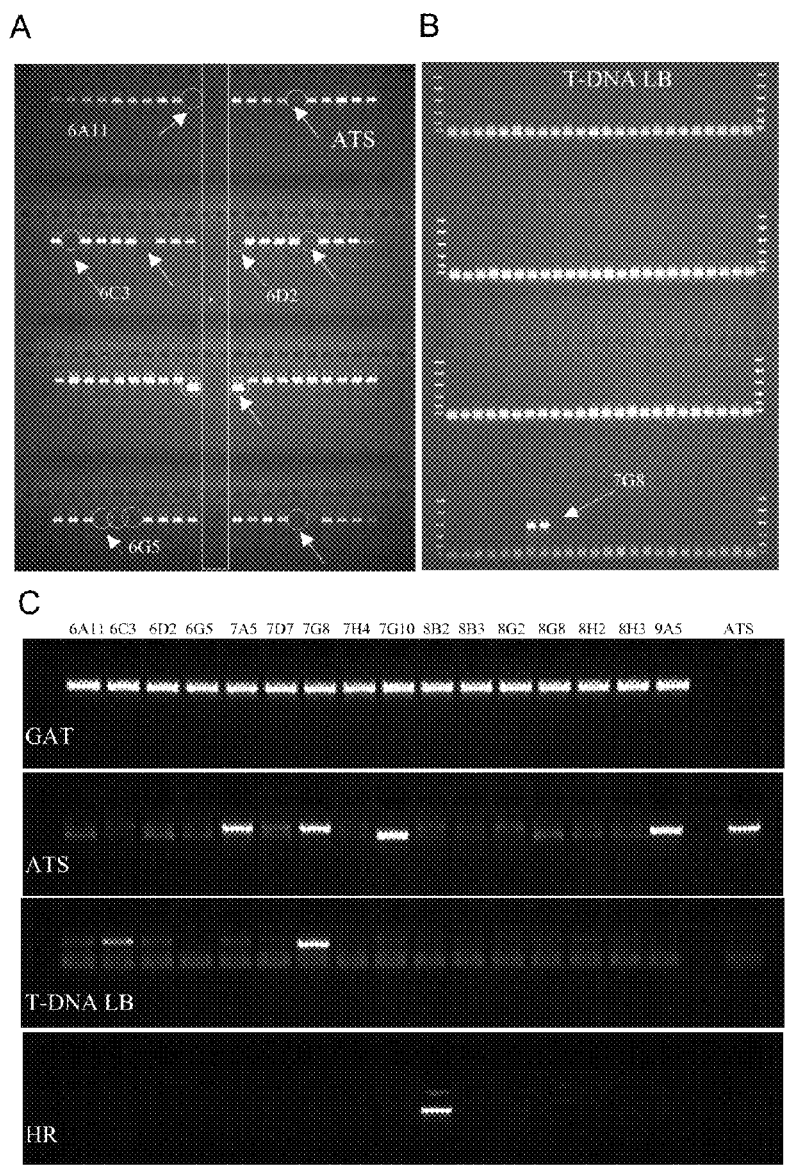
FIG. 4. PCR screening for target site mutations, T-DNA insertions, and homologous recombination events from PHP27031. (A) Initial PCR with primers to ATS. White arrows point to the events selected for further PCR analysis. (B) PCR to identify junction sites between target site and T-DNA LB (LB PCR). White arrows point to the PCR reactions that yielded the expected product. (C) PCR screening of re-transformation events selected in the first round of PCR reactions. Amplification of the internal fragment of the GAT coding sequence used to validate DNA template preparations (GAT panel). The HR panel shows an example of a homologous recombination product (lane 8B2). Lane ATS is control DNA template from the original target line 2248.
Figure 5:
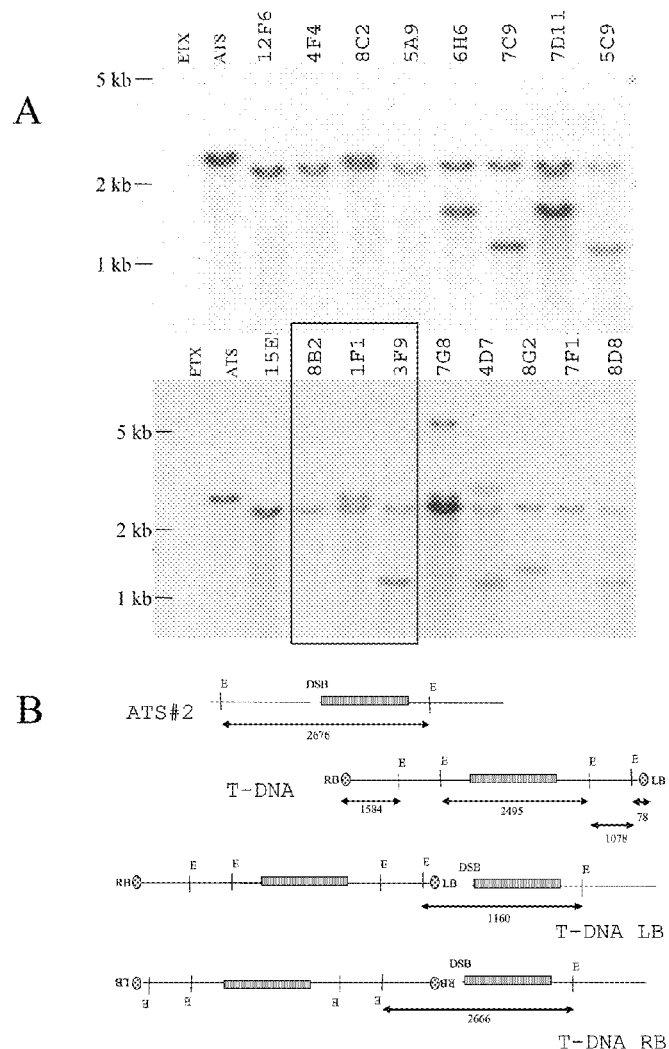
FIG. 5. (A) Southern blot analysis of selected re-transformation events. Total leaf DNA (10 μg) digested with EcoRI was separated on 0.7% agarose gels, and hybridized with the YFP probe. The sizes of the expected bands hybridizing with the YFP probe are shown in diagram B. Control DNA from untransformed maize is shown in lane "ETX", and "ATS" contain control DNA from target line 2248. All re-transformed plants should contain the 2.5 kb fragment originating from the targeting T-DNAs. The original ATS 2.7 kb fragment was not detected except in event 1F1 and 7G8 DNA preparations. The 1.16 kb fragments hybridizing to the YFP probe were diagnostic of the T-DNA left border junction with the right side of the I-SceI double-strand break. The T-DNA right border junction site should produce the 2.6 kb fragment identified in the lane 8C2.7G8 shows a relatively strong 2.5 kb band which could result from additional deletions within the right border junction site overlapping with the T-DNA band, which was confirmed by subsequent sequencing of the right border junction site in the 7G8 event (FIG. 6). The presence of just one 2.5 kb band originating from T-DNA is a strong indicator of ATS homologous recombination events using T-DNA as a template (see, for example, lanes 12F6, 4F4, 5A9, 15E5, 8B2, or 7F11).

The PCR-based screening procedure was validated by Southern blot analysis and sequencing of a subset of selected events. PHP27031 samples having 2 EcoRI fragments hybridizing to the YFP probe, 2.7 kb band for ATS, and 2.5 kb band for T-DNA, indicated a random insertion of T-DNA without a substantial modification of ATS2 (for example, lane 1F1, FIG. 4). The target site was sequenced in this plant to validate the structure of ATS2 (FIG. 5). Among the 36 PHP27031 plants tested, seven plants showed both the 2.7 kb and the 2.5 kb band hybridization pattern. The hybridization patterns of the remaining 29 plants indicated some significant alteration to ATS2 had occurred. Left border ligation into the right side of the I-SceI double-strand break (as depicted in FIG. 4) should produce a 1.16 kb EcoRI fragment. Ten plants showed this hybridization pattern, for example, lanes 7C9, 5C9, 3F9, 4D7, 8D8 (FIG. 4). The junction sites were further evaluated by sequencing as documented for the 3F9, 1H1, or 4D7 events (FIG. 5). The right border ligation in the same orientation produced the EcoRI fragment similar in size to the ATS2 hybridization band (for example, lane 8C2 in FIG. 4). Four such events were confirmed by sequencing; plants 8C2, 8C6, 8F7, and 7G8 (FIG. 5). The latter event (7G8) indicated more complex rearrangement of ATS2 by PCR and Southern blot analysis (FIGS. 3 and 4). Eight plants showed just one EcoRI 2.5 kb fragment corresponding to the T-DNA vectors. These plants were classified as homologous recombination events, for example, lanes 12F6, 4F4, 5A9, 15E5, 8B2, 7F11 (FIG. 4). The PHP27031 homologous recombination events were confirmed by sequencing in plants 12F6, 15E5, and 8B2 (FIG. 4C). Other plants showed more complex hybridization patterns or rearrangements that were difficult to interpret, for example, lanes 7G8, 6H6, 8G2, or 7D11 (FIG. 4).

FIG. 5 shows the junction sites between T-DNA borders and the I-SceI restriction sites in a PHP27031 event. Unlike sequenced mutations at the I-SceI site, the junctions at T-DNA left border did not contain an example of the 4 bp overhang (ATAA) in the recombinant products. Instead, both ends showed deletions to varied degrees. We found the 3' overhang sequence when the right border of T-DNA ligated to the right side of the I-SceI site. The 8C6 event from PHP27031 showed a perfect ligation of the right border to the 3' overhang (FIG. 5, T0 T-DNA RB), while the 8F7 event showed a short 4 bp deletion at the right border. The complexity of the 7G8 event was extended into the RB-I-SceI junction site showing long 158 bp deletion and 10 bp insertion of an unknown DNA fragment. Interestingly, we observed only one integration pattern for the right border of T-DNA ligated into the left side of the I-SceI site. The right border sequence was left intact, while three nucleotides of the 3' overhang were removed. The 3F9 event demonstrates the T-DNA junction sequences at both ends.

Figure 6:
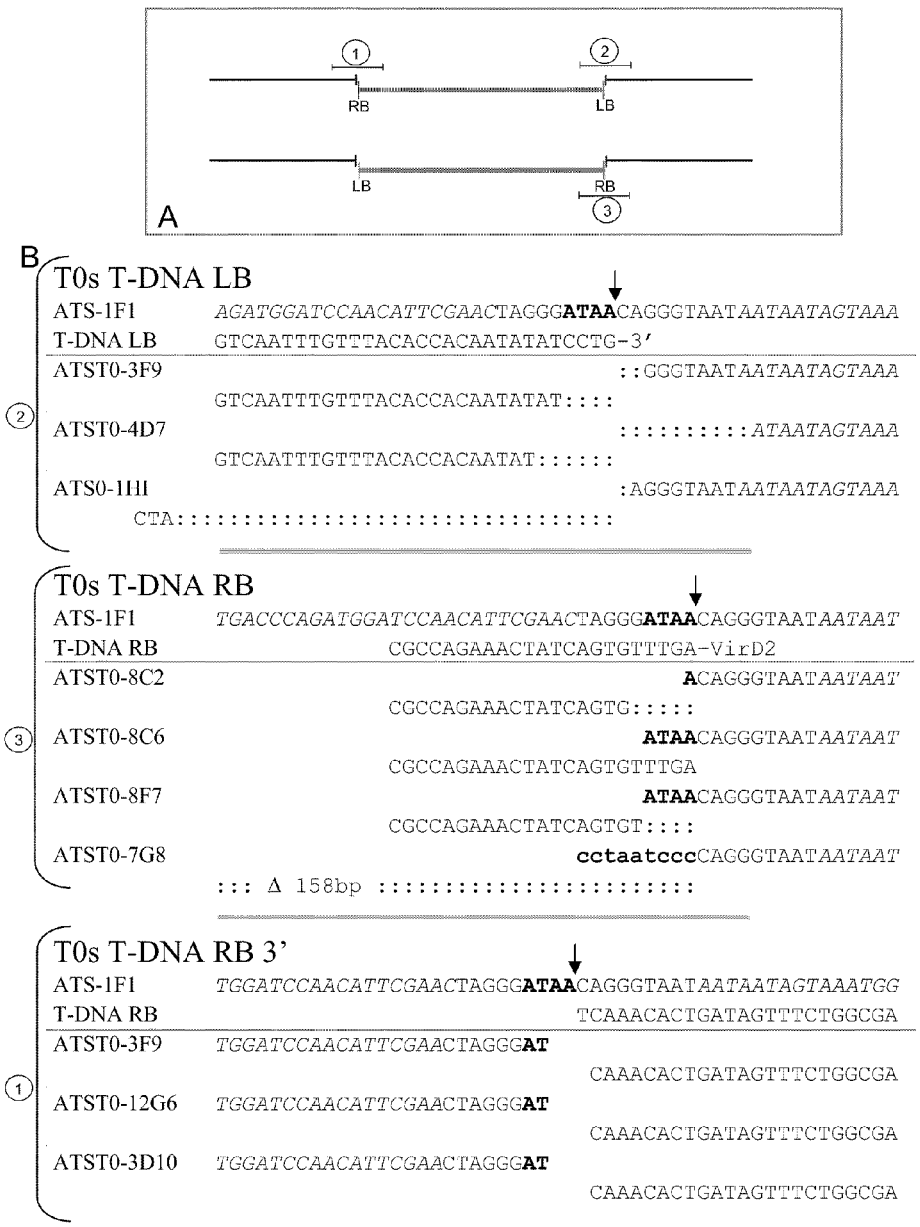
FIG. 6. Nucleotide sequence of the T-DNA border and target site junctions from I-SceI-produced double-strand breaks in events from PHP27031. The codes and annotations are same as used in FIG. 2. The original ATS target site was sequenced from event 1F1 and is shown at the top of each panel. Shown immediately below are the left border (T0s T-DNA LB) and right border (T0s T-DNA RB) sequences aligned to produce the complete ligation products (no deletions or insertions). The lower panel (T0s T-DNA RB 3') shows predicted and observed ligation products of the right border to the upper strand 3' overhang of the double-strand break. Only a single strand of T-DNA (the strand with VirD2 protein attached) was used for these alignments; however this does not imply that the other strand is not involved in the integration process.
Figure 7:
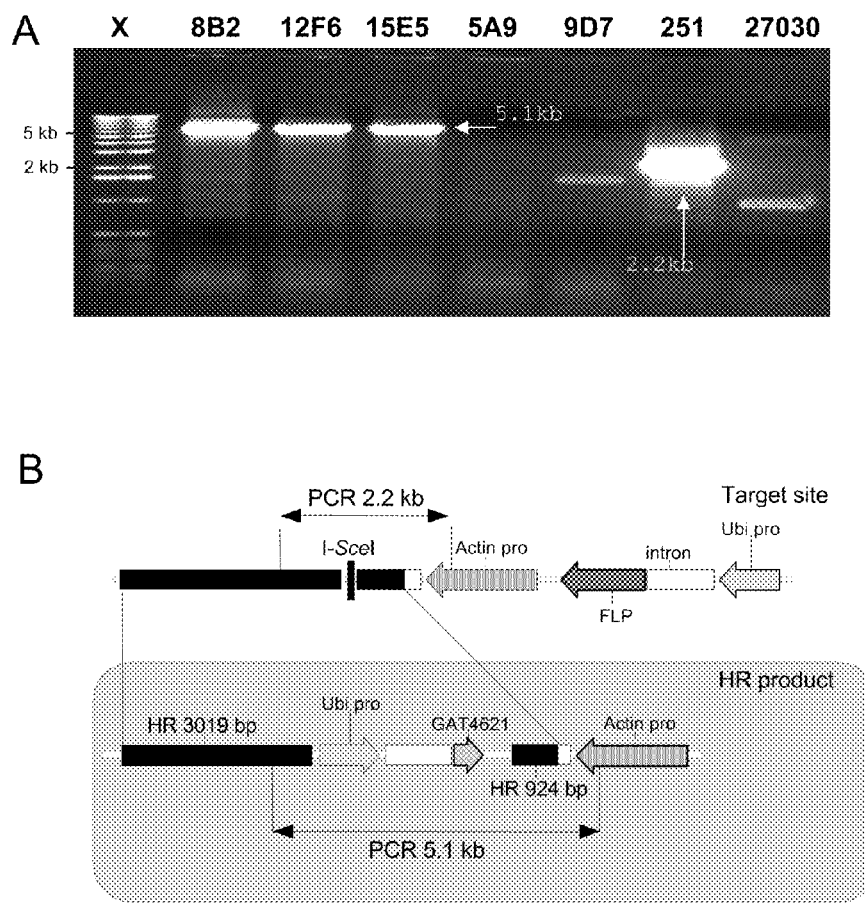
FIG. 7. PCR verification of target site modifications in selected PHP27031 retransformation events. (A) The PCR products were obtained from three putative homologous recombination events (8B2, 12F6, 15E5). Fragments of about 5 kb correspond to the predicted size of a fragment containing a GAT insertion into the target (See B). Lane 251 shows a PCR product of about 2 kb, as expected from the original target site, confirming the Southern blot analysis for this event. All three fragments were cloned into TOPO vectors and sequenced to confirm that they are homologous recombination events.
Figure 8:
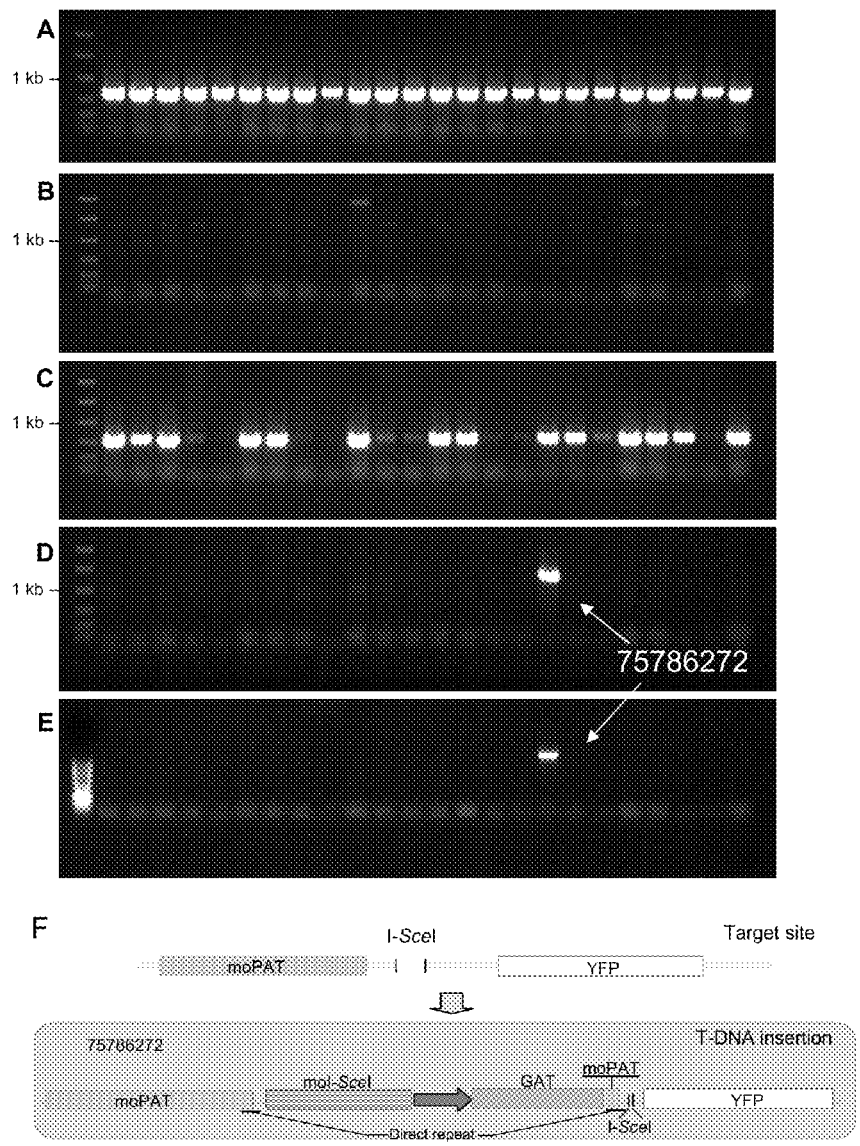
FIG. 8. PCR screening of ATS2 null events from PHP30662. (A) PCR with ADH1 control (B) PCR for ATS2 site (C) PCR for YFP coding region (D) PCR for GAT and YFP coding regions (E) PCR for PAT and I-SceI coding regions (F) diagrammatic representation of possible insertion product.

Three homologous recombination events from PHP27031 were sequenced using template obtained by PCR amplifying the entire ATS2 locus modified by homologous recombination. PCR primers were specific to the rice actin promoter and the YFP coding sequence (FIG. 6). The 5.1 kb product was recovered in three events which were identified as HR events, while the 2.2 kb product was recovered from event 251 previously shown to contain unchanged ATS2. We did not recover a 5.1 kb fragment from two pre-identified HR events 5A9 and 9D7 for unknown reasons (compare FIG. 4 and FIG. 6). It was found that the GAT selectable marker gene was inserted into the ATS2 site precisely as expected for homologous recombination products between ATS2 and the homology regions flanking the GAT gene on T-DNA molecules for all 3 events sequenced (sequencing data not shown).

The selected T-DNA insertion and homologous recombination putative events from PHP27031 were grown to maturity and test crossed to non-transgenic parental plants. Typically the outcrossed T-DNA integration and homologous recombination events produced progeny as expected for a single modified ATS locus. Whether the GAT gene was inserted by T-DNA integration or homologous recombination, in all cases the gene was placed in the ATS2 locus.

Regardless of whether the two ends of a double-strand break are ligated together or T-DNA ends are involved in the repair process, the structural features of the junction products appear to be similar, which may indicate that similar DNA repair pathways are involved. Deletions at the T-DNA left border are more pronounced compared to the right border, which is consistent with T-DNA integration patterns observed in other plants (Kumar and Fladung, (2002) *Plant J* 31:543-51), including T-DNA integration at artificially produced double-strand breaks (Chilton and Que, (2003) *Plant Physiol* 133:956-65; Tzfira, et al., (2003) *Plant Physiol* 133:1011-23). Similar patterns of T-DNA integration were also observed in a survey of transgenic rice events (Kim, et al., (2003) *Plant Mol Biol* 52:761-73). We also found the I-SceI 3' overhang sequence in the repair products and at the T-DNA right border junctions, but not at T-DNA left border junction sites in samples that were sequenced. In contrast, the 3' overhangs were observed in the T-DNA left border junctions at the I-CeuI restriction sites in tobacco (Chilton and Que, (2003) *Plant Physiol* 133:956-65). We found examples of microhomologies at the junction sites, and also direct ligations without overlaps or filler DNA were also identified (FIG. 5, 3F9 event).

The PCR-based screening procedure identified major rearrangements of ATS2, as indicated by the lack of any amplification product, or PCR products of different size, in about 4% of analyzed re-transformation events from PHP27031 (53/1380). For PHP27031, 36 selected events were further characterized by Southern blots with 8 events hybridizing to a 2.7 kb EcoRI digestion fragment putatively comprising a T-DNA insertion by a homologous recombination reaction. Three of these events were sequenced to confirm that they were produced by homologous recombination between ATS2 and T-DNA. The homologous recombination product was faithfully transmitted to the T1 testcross generation, segregating 1:1 and showing genetic linkage between the T-DNA fragment (the GAT gene) and the ATS2 border sequence (the FLP gene). These results demonstrate that T-DNA can integrate through homologous recombination pathways at maize chromosomal locations marked by the I-SceI-introduced double-strand breaks.

For PHP30662, overall 836 glyphosate resistant plants were generated and at least partially characterized. From these about 80% of glyphosate resistant events from PHP30662 showed evidence of some DNA rearrangement near the ATS2 site by PCR, indicating that regions of homology do not significantly affect the frequency of double-strand break induction and/or repair at the ATS2 site. The ATS2 site is amplified using primers to moPAT and YFP regions. From 836 analyzed plants, 92 plants are ATS2 null by PCR. From these 92 ATS2 null plants, about 46% (42/92) retained the YFP coding region as determined by PCR for YFP, however only about 9% (8/92) of these ATS2 null events retained the moPAT coding region as determined by PCR for moPAT. It was expected that a T-DNA insertion at the double-strand break without other major rearrangements would be ATS2 null by PCR, YFP+ and moPAT+ by PCR. Four putative insertion events were identified by PCR, one event (75786272) has been confirmed by sequencing to be a T-DNA insertion at the I-SceI recognition site.

Example 2

Any plant transformation method can be used to produce a target line, provide the double-strand break inducing agent, and/or provide one or more polynucleotide constuct(s) comprising a polynucleotide of interest.

A. Particle Bombardment Transformation and Regeneration

Any available tissue sources, culture media, construct preparations, particle preparation methods, and bombardment methods can be used with the compositions and methods provided herein.

1. Maize

Immature maize embryos from greenhouse or field grown High type II (HiII) donor plants are bombarded with at least polynucleotide construct described above. If the construct does not include a selectable marker, another polynucleotide containing a selectable marker gene can be co-precipitated on the particles used for bombardment.

Ears are harvested 8-12 days after pollination for the isolation of fertilized embryos. The harvested ears are surface sterilized in 50% Chlorox™ bleach plus 0.5% Micro detergent for 20 minutes, then rinsed twice with sterile water. The immature embryos are excised and placed embryo axis side down (scutellum side up), 25 embryos per plate. These are cultured on 560L agar medium 4 days in the dark prior to bombardment. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

Particles are prepared by precipitating the DNA to be delivered onto 1.0 μm (average diameter) gold pellets using a $CaCl_2$ precipitation procedure as follows: 100 μl prepared gold particles (0.6 mg) in water, 20 μl (2 μg) DNA in TrisEDTA buffer (1 μg total), 100 μl 2.5 M $CaCl_2$, 40 μl 0.1 M spermidine. Each reagent is added sequentially to the gold particle suspension. The final mixture is sonicated briefly. After the precipitation period, the particles are centrifuged briefly, washed with 500 μl 100% ethanol, pelleted again and resuspended in 60 μl 100% ethanol to make the final suspension. Macrocarriers are prepared by briefly sonicating the final preparation, spotting 5 μl onto the center of each macrocarrier, and drying for about 2 minutes before bombardment. The sample plates are bombarded at a distance of 8 cm from the stopping screen to the tissue, using a DuPont biolistics helium particle gun. All samples receive a single shot at 650 PSI, with a total of ten aliquots taken from each tube of prepared particles/DNA.

Alternatively, DNA to be delivered is associated with microparticles using a reagent comprising a cationic lipid solutions. For example, DNA solutions are added to 50 μl of a gold-particle stock solution (0.1 μg/μl of 0.6 micron gold particles). A DNA stock, 10 μl of a 0.1 μg/μl plasmid solution, is added to 30 μl of water. To this DNA mixture, 50 μl of the gold stock solution is added and the mixture briefly sonicated. Next 5 μl of TFX-50™ (Promega Corp, Madison Wis.) is added, and the mixture is placed on a rotary shaker at 100 rpm for 10 minutes. The mixture is briefly centrifuged to pellet the gold particles and remove supernatant. After removal of the excess DNA/TFX solution, 120 μl of absolute EtOH is added, and 10 μl aliquots are dispensed onto the macrocarriers typically used with the DuPont PDS-1000 Helium Particle Gun. The gold particles with adhered DNA are allowed to dry onto the carriers and then these are used for standard particle bombardment.

Four to 12 hours post bombardment, the embryos are moved to a low osmoticum callus initiation medium for 3-7 days, then transferred to selection medium and subcultured every 2 weeks. After about 10 weeks, embryos are transferred to regeneration media. Following 2-4 weeks of somatic embryo maturation, well-developed somatic embryos are transferred to germination medium in a lighted culture room. Approximately 7-10 days later, developing plantlets are transferred to tubes until plantlets are well established and can be transplanted into flats and/or pots and grown to maturity.

2. Rice

Sterilized rice seeds are germinated on a callus initiation media in the dark at 27-28° C. Embryogenic callus proliferating from the scutellum of the embryos is then transferred to CM media (Chu, et al., (1985) *Sci Sinica* 18:659-668) and maintained by routine sub-culture at two week intervals. These embryonic cultures are used for transformation within 10 weeks of initiation. Callus is prepared for transformation by subculturing 0.5-1.0 mm pieces approximately 1 mm apart, arranged in a circular area of about 4 cm in diameter, in the center of a circle of Whatman #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate. The petri dish containing the tissue is placed in the PDS-1000/He chamber approximately 8 cm from the stopping screen. The chamber is evacuated to 28-29 inches Hg, and the particle macrocarrier accelerated with a helium shock wave using a rupture membrane that bursts when the pressure reaches 1080-1100 psi. Each plate is bombarded two times. Following bombardment, the callus tissue is transferred to CM media without supplemental sorbitol or mannitol. Within 3-5 days after bombardment the callus tissue is transferred to CM media containing 50 mg/l hygromycin. The callus is transferred to 50 ml conical tubes, weighed, and top-agar at 40° C. is added (2.5 ml of top agar/100 mg of callus). Callus clumps are broken into fragments of less than 2 mm diameter using a sterile 10 ml pipet. Three ml aliquots of the callus suspension are plated onto fresh media and the plates incubated in the dark for 4 weeks at 27-28° C. After 4 weeks, transgenic callus events are identified, transferred to fresh media plates and grown 2 weeks in the dark at 27-28° C. Growing callus is transferred to RM1 media (MS salts, Nitsch & Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch & Nitsch vitamins, 3% sucrose, 0.4% gelrite; 50 ppm hyg B) and placed under cool white light (~40 μEm−2s−1) with a 12 hr photoperiod at 25° C. and 30-40% humidity. After 2-4 weeks the callus generally begins to form shoots, which are gently transferred to RM3 media (½×MS salts, Nitsch & Nitsch vitamins, 1% sucrose; 50 ppm hygromycin B) in phytatrays (Sigma Chemical Co., St. Louis, Mo.) and grown under the RM2 conditions above. When sufficient root and shoot growth has occurred, plants are transferred to potting media and grown using a 12 hr/12 hr light/dark cycle using ~30/18° C. day/night temperature regimen.

B. *Agrobacterium*-Mediated Transformation and Regeneration

Any available embryo/tissue source, culture media, construct preparation, particle preparation method, and bombardment method can be used with the compositions and methods provided herein.

1. Maize

*Agrobacterium* mediated transformation of maize is performed essentially as described by Zhao, et al., (WO98/32326). Briefly, immature embryos are isolated from maize and the embryos contacted with a suspension of *Agrobacterium* containing a T-DNA, where the bacteria are capable of transferring the nucleotide sequence of interest to at least one cell of at least one of the immature embryos.

Step 1: Infection Step. In this step the immature embryos are immersed in an *Agrobacterium* suspension for the initiation of inoculation.

Step 2: Co-cultivation Step. The embryos are co-cultured for a time with the *Agrobacterium*.

Step 3: Resting Step. Optionally, following co-cultivation, a resting step may be performed. The immature embryos are cultured on solid medium with antibiotic, but without a selecting agent, for elimination of *Agrobacterium* and for a resting phase for the infected cells.

Step 4: Selection Step. Inoculated embryos are cultured on medium containing a selective agent and growing transformed callus is recovered. The immature embryos are cultured on solid medium with a selective agent resulting in the selective growth of transformed cells.

Step 5: Regeneration Step. Calli grown on selective medium are cultured on solid medium to regenerate the plants.

2. Sorghum

*Agrobacterium* mediated transformation of maize is performed essentially as described by Cai, et al., (WO98/49332). *Sorghum* immature embryos about 0.8-1.5 mm are isolated from surface sterilized immature sorghum kernels using a sterile spatula. The isolated embryos are cultured on medium without acetosyringone in the dark at about 25° C. for 5 days. These precultured embryos are inoculated with 109 cfu/ml *Agrobacterium* suspension using 1 ml of *Agrobacterium* suspension/100 embryos, mixed, and incubated 5 min at room temperature. The *Agrobacterium*-embryo suspension is poured onto a petri plate containing co-cultivation medium. The *Agrobacterium* suspension is removed and the embryos oriented axis side down on the media. The plates are sealed and incubated in the dark at about 25° C. for about 5 days of co-cultivation. The embryos are transferred to new plates with selection media, sealed, and incubated in the dark at 25° C. for two weeks. The embryos are transferred to fresh selection medium every 2-3 weeks for a total of about 3.5 months to obtain herbicide-resistant calli. Selected callus is cultured on regeneration medium in the dark at 28° C. for 1-3 weeks to allow somatic embryos to mature. Plantlets are generated by transferring the callus to a shoot medium at 25° C. under a 16:8 hour day:night schedule (daylight 270 µE m−2sec−1) until shoots and roots develop. Each plantlet is transferred to a tube containing shoot medium, grown under the same conditions for approximately another week until large enough to transplant to soil.

Example 3

A. Maize Codon-Modified I-SceI

A vector containing an open reading frame encoding I-SceI derived from a *S. cerevisaie* coding region was obtained from Cellectis S.A. (Romainville, France) was screened for sequence motifs, GC/AT composition, and restriction sites. Adjustments to the codon usage, GC content, removal of possible processing and/or destabilization sequences, and other modifications can improve the efficiency of expression of a heterologous gene in a target organism. Typically these changes can be introduced with very few or no amino acid substitutions in the encoded protein (see, for example, U.S. Pat. No. 5,567,600; Boudraa, (1987) *Genet Sel Evol* 19:143-54; Grantham, et al., (1985) *Bull Inst Pasteur* 83:95-148; and WO 2006/107954). After evaluation and codon modification, a mo-ISceI ORF was designed with 56% GC, without HindIII, PvuII, or PvuI restriction site, and linkers were added to facilitate cloning. The modified version of I-SceI coding sequence was synthesized by DNA 2.0 (Menlo Park, Calif., USA). The original cloning vector produced was PHP26686. PHP26987 was generated from PHP26686 by removal of a NotI restriction site to produce the moI-Sce coding region used (SEQ ID NO: 1). This vector was cut with BamHI/PacI, and the moI-SceI fragment ligated into the corresponding sites of PHP26440 to produce the moI-SceI expression vector PHP26603 (ubi pro::moI-SceI) used for subsequent experiments and vector constructions.

Verification of moI-SceI expression was done using transient bombardment assays. Activation of YFP expression in bombarded maize embryos was used as an indicator of I-SceI expression and double-strand break activity. The tester vector, PHP22569, contained the I-SceI recognition site separating two overlapping fragments of YFP coding region. A double-strand break produced by I-SceI activated the repair process, putatively the single-strand annealing (SSA) homologous recombination pathway, leading to activation of YFP expression as monitored using a fluorescence microscope under the appropriate filters. The results of these experiments demonstrated that the moI-SceI sequence and expression vectors were functional.

Example 4

A. Maize A TS2 Lines, Characterization, and Selection

A vector comprising an artificial target site (ATS) having a recognition sequence for double-strand break inducing agent I-SceI was constructed using standard molecular biology techniques and used for maize transformation. Unlike constructs and strategies typically employed, the ATS does not comprise a fragment of a selectable marker expression cassette used to identify/select plant cells having the modification. The ATS optionally has a phenotypic marker used to identify events comprising the target site.

ATS2 was designed to minimize the presence of maize-derived sequences in order to facilitate interpretation of the results. Flanking 5' and 3' homology regions of about 1 kb and about 4.1 kb respectively were provided for homologous recombination experiments. The 5' homology region comprises a moPAT sequence, and the 3' homology region comprises a YFP sequence plus addition of 1578 bp of non-coding genomic sequence from *Arabidopsis* (gAt) following the pinII terminator. The I-SceI recognition site and 3 stop codons are located between the moPAT and YFP coding regions. A FLP expression cassette was included for testing other vector and experimental design strategies. ATS2 vector PHP22709 comprises the following operably linked components:

Ubi pro::FLPm-rice actin pro::moPAT/I-SceI site/STOP/ YFP::pin II-gAt

Transient transformation tests of Hi-II embryos bombarded with PHP22709 showed no visible yellow fluorescence indicating that translation of YFP was stopped as expected. Stable maize plant lines having ATS2 were generated by transforming 9-12 DAP Hi-II immature embryos (1-1.5 mm in size) with vector PHP22709 using *Agrobacterium*-mediated methods essentially as described in Example 2B1.

A total of 20 T0 ATS2 stable transgenic plants were generated, 19 of which survived to maturity. Leaf samples from these plants were collected for Southern analysis. Only single copy events that produced greater than 10 T1 kernels were used for further experiments. Twelve T0 events were identified from this process. T1 seeds produced by T0 self pollinations were planted for further characterization to confirm single copy ATS2 events by T1 segregation analysis. Bar gene activity was determined using a BAR protein detection kit. Four events (59, 60, 99, and 102) showed 1:2:1 Mendelian segregation for the ATS2. Events 99 and 102 also showed 3:1 segregation for BAR expression, showing that the selected events were transcriptionally active. A total of 68 homozygous plants were produced from six selected single copy events and moved to the greenhouse for seed and embryo production for transformation. Of the six selected events, event 59 and 99 showed a good tassel/ear developmental coordination. Embryos from these two events were used for a FLP activity assay to further confirm that the target site was transcriptionally active and to verify FLP function. PHP10968 is a FRT excision test vector comprising ubi pro:: FRT1::GFP::FRT1::uidA coding sequence. FLP-mediated excision of the GFP fragment is expected to reconstitute the GUS expression. Every embryo from these events showed GUS activity, indicating that ATS2 sites in the two independent events were transcriptionally active.

A total of six homozygous, single copy transgenic maize lines containing the ATS2 fragment were produced. Two were used for initial screening for alterations including sequence alterations and/or T-DNA insertions at the I-SceI site in two preliminary re-transformation experiments, one of these was selected for any further experiments. The selected ATS2 homozygous line was outcrossed to non-transgenic parental plants in order to produce ATS2 hemizygous embryos which were subsequently used in re-transformation experiments.

Example 5

Any standard protocol for isolation, manipulation, and characterization of polynucleotides and or proteins can be used to identify, select, and characterize putative modification events.

A. PCR

For high-throughput PCR screening of large numbers samples, DNA was extracted by a HotSHOT protocol (Truett, et al., (2000) *Biotechniques* 29:53-54). Briefly, one leaf punch, or equivalently sized sample, 400 µl of extraction buffer (25 mM NaOH, 0.2 mM EDTA), and two stainless steel beads were placed in each tube of a Mega titer rack. The samples were ground and extracted by shaking in a Genogrinder at 1650 rpm for 30-60 seconds, then incubated for 60-90 minutes at 95° C. The extracts were cooled to room temperature, 400 µl neutralization buffer (40 mM Tris-HCl, pH 5.0) added, and shaken at 500 rpm for 20-30 minutes. The samples were centrifuged at 4,000 rpm for 5-10 minutes, supernatant removed and pellets discarded. Two µl of the supernatant for each sample was used for PCR.

For further evaluation of putative events, DNA was extracted using the Qiagen Dneasy Plant Mini kit according to the provided protocol (Qiagen Inc., Valencia, N. Mex., USA). PCR reactions contained 2 µl of DNA extract (100-200 ng), 10 µl of RedExtractandAmpPCR mix (R4775, Sigma, St. Louis, Mo.), 0.05 µl of each primer at 100 µM concentration, and 7.9 µl water. The Expanded Long Template PCR amplification system (Roche Molecular Biochemicals, Indianapolis, Ind.) was used to amplify products of about 3 kb or larger. The Eppendorf Mastercycler Gradient cycler (Eppendorf North America, Westbury, N.Y.) was used, the PCR programs varied depending on primer annealing temperature and length of the PCR product. PCR products were evaluated and purified by agarose gel electrophoresis, by loading 15 µl of each PCR reaction and 1% agarose gel. PCR products were purified using Qiagen PCR purification kit (Qiagen Inc., Valencia, N. Mex.).

The following PCR primer pairs were used:

```
1. ATS2 primers:
(SEQ ID NO: 3)    104797 5'-TCGTGAACCACTACATCGCGACCTC;
and, (SEQ ID NO: 4)    104798 5'-AGCAGCTTGTGCTGGATGAAGTG 2. I-SceI recognition site primers (in ATS2):
(SEQ ID NO: 5)     59723 5'-TCTTGCTGGGCACGCTCTTG;
and, (SEQ ID NO: 6)    104381 5'-GGTCTCGATCTTTGGCCTTGGTAGT 3. HR primers:
(SEQ ID NO: 7)    124641 5'-TAAGATTAAAATAGCTTTCCCCCGTTGCAGCGC;
and, (SEQ ID NO: 8)    104798 5'-AGCAGCTTGTGCTGGATGAAGTG 4. LB primers set 1: (T-DNA insertion)
(SEQ ID NO: 9)    104801 5'-TTCGAAGATCTGCCCACTAGTGAGTC;
and, (SEQ ID NO: 10)   104798 5'-AGCAGCTTGTGCTGGATGAAGTG
```

5. LB primers set 2: (T-DNA insertion)
(SEQ ID NO: 11)   104381 5'-GGTCTCGATCTTTGGCCTTGGTAGT;
and, (SEQ ID NO: 12)   124437 5'-CTTGTTGAACGCCTGGTGCTTGAAGGTCTG 6. RB primers: (T-DNA insertion)
(SEQ ID NO: 13)   124437 5'-CTTGTTGAACGCCTGGTGCTTGAAGGTCTG;
and, (SEQ ID NO: 14)   104798 5'-AGCAGCTTGTGCTGGATGAAGTG B. Southern Blot Selected events were further analyzed by Southern blots. Leaf tissue (about 1-2 grams fresh weight) was grounded into a fine powder with liquid nitrogen. Twenty ml Puregene® Cell Lysis Solution was added to each sample and incubated 1 hr at 64° C. while shaking at 750 rpm. Samples were centrifuged 10 minutes at 4,000 rpm. DNA extract supernatants were transferred to new tubes, mixed with 5 ml of phenol/chloroform (1:1) solution, and centrifuged 10 minutes at 4,000 rpm. The upper phase was removed, and mixed with an equal volume of isopropanol to precipitate the DNA. The solutions were centrifuged 10 min at 4000 rpm, supernatant removed, and the pellets resuspended in 5 ml of TE buffer, pH 8.0, 0.4 ml of ethidium bromide (10 mg/ml), and 5 g of cesium chloride. The mixture was centrifuged overnight (12-17 hrs) at 390,000 g. The DNA extraction and ethidium bromide removal were done essentially as described in Sambrook, et al., (1989) *Molecular Cloning: A Laboratory Manual*, Cold Spring Harbor Laboratory Press, NY. The final DNA preparations were dissolved in TE buffer to yield 1.0 µg/µl DNA solutions. Ten µg DNA from each sample was digested overnight with 50 units of selected restriction enzyme(s) and digestion product(s) separated in 0.7% agarose gel run at 35 mV overnight. The TurboBlotter and Blotting Stack (Schleicher and Schuell, Keene, N.H.) were used to transfer DNA onto a nylon membrane as described in the manufacturer's manual. The DNA fragments were attached to the membrane by UV irradiation at 1.2 kjoules/m$^2$ in the UV Stratalinker (Stratagene, Cedar Creek, Tex.). The blots were pre-hybridized 2-3 hrs in 20 ml of ExpressHyb hybridization solution (Clontech, Palo Alto, Calif.) at 65° C. The random prime labeling system (Amersham Pharmacia Biotech, Piscataway, N.J.) was used with Redivue [$^{32}$P]dCTP to produce radioactively labeled DNA fragments according to the supplied protocol. Hybridizations were incubated overnight at 65° C. Blots were washed twice with 1% SSCE/0.1% SDS solution for 15 min at 65° C., followed by two additional washes with 0.1% SSCE/0.1% SDS under the same conditions.

C. Sequencing

PCR products produced from DNA isolated using Qiagen Dneasy Plant Mini kit and amplified as described above where used for sequencing reactions. PCR products less than 4 kb were directly sequenced, or cloned into the pCR4-TOPO vector (InVitrogen, Carlsbad, Calif., USA). Longer PCR products were first cloned into a vector and then used for sequencing. Selected putative targeting events were further characterized by DNA sequencing using with BigDye Terminator chemistry on ABI 3700 capillary sequencing machines (Applied Biosystems, Foster City, Calif.). Each sample contained either 0.4-0.5 µg plasmid DNA or about 10 ng of the PCR products, and 6.4 pmole primer. Sequences were analyzed using the Sequencher™ program (Gene Codes Corp., Ann Arbor, Mich., USA).

D. Nuclease Digestion of PCR Product

PCR products amplified using primers directed to the target site were purified by Qiaquick. The double-strand break inducing enzyme or a restriction enzyme contained in the target site was added to the purified target site PCR product DNA to test if the target site had been modified. This mixture was digested at 37° C. for about 0.5 hr to 5 hr, the digestion time depending on the enzyme used. Samples with meganuclease enzyme were treated with 0.5 µl proteinase K and 0.2 µl 20% SDS to denature the protein. Samples with MluI were not treated with proteinase K or SDS. The digestion products were separated on a 1.5 to 2% agarose gel. Undigested products indicate that the target site was modified. See, for example, FIG. 2.

SUMMARY

Using the ATS2 lines, vectors, and methods described above all possible products were observed after inducing double-strand breaks, including sequence modifications, T-DNA insertions, and homologous recombination products. This was possible because the transformation and screening of events did not rely on the reassembly of a functional selectable marker expression cassette, instead vector delivery was confirmed and putative events directly screened by PCR assays, Southern blots, and/or sequencing. Approximately 80% of all glyphosate-resistant T0 events showed indications of a modification of the ATS2/I-SceI site as indicated by resistance to I-SceI digestion. These ATS2 modifications were predominantly sequence alterations such as nucleotide deletions, additions, and/or substitutions.

Sequencing of these events at the T0 and the T1 generations confirmed that the modifications were stably inherited. We also identified T-DNA insertions at the ATS2 site, which typically showed the predicted T1 segregation ratio for GAT when outcrossed to a non-transgenic line. Sequencing of the border junctions of T-DNA inserts typically showed small sequence alterations such as nucleotide deletions, and/or additions of the border and/or I-SceI sequences, similar to sequence alterations observed for T-DNA insertions in plants under standard, random transformation methods. More complex rearrangements, deletions, and/or additions were also observed, however these are also observed in other *Agrobacterium*-mediated transformation events in plants.

Homologous recombination events have been isolated from TV-ATS2 transformants, and typically showed the predicted T1 segregation ratio for GAT when outcrossed to a non-transgenic line as noted for T-DNA insertion events. Based on preliminary results and characterization of TV- ATS2 events indicating significant modification of ATS2 by PCR, and further Southern analysis of 36 of these events the following was observed: 7/36 showed random insertion of T-DNA with no significant alteration to ATS2; 8/36 showed DNA insertion by homologous recombination at the I-SceI break site; 10/36 showed T-DNA insertion at the I-SceI site apparently by non-homologous recombination DNA repair; and 11/36 showed other non-homologous recombination DNA repair products and/or complex products.

Table 3 provides a summary of the vectors tested by retransformation of maize ATS2-containing embryos, and the types of modification products observed.

TABLE 3

| Vector | Vector elements | | #plants analyzed | DSB site modifications | | |
| --- | --- | --- | --- | --- | --- | --- |
| | I-SceI? | Homology? | | Mutation | Non-HR | HR |
| 22066 | No | No | 123 | No | No | No |
| 30662 | Yes | No | 836 | Yes | Yes | No |
| 27031 | Yes | Yes | 1380 | Yes | Yes | Yes |

Example 6

Maize lines comprising an endogenous target recognition sequence in their genome were contacted with an engineered meganuclease derived from I-CreI designed to specifically recognize and create a double-strand break in the endogenous target sequence. Immature embryos comprising an endogenous target site were contacted with the components described below, events selected and characterized.

A. LIG3-4 Target Site

An endogenous maize genomic target recognition sequence, referred to as LIG3-4, was selected for design of a custom double-strand break inducing agent derived from I-CreI meganuclease.

The genomic region comprising the LIG3-4 recognition site has the following sequence, with the LIG3-4 target recognition site shown in bold:

```
                                               (SEQ ID NO: 15)
CTTCTTTTGATCGGCTGCGGAAATAATATACTGTAACGATTTACGCACCT

GCTGGGAATTGTACCGTACGTGCCCCGGCGGAGGATATATATACCTCACA

CGTACGCGTACGCGTATATATACGTGCGCTGCTACTCATTTGCGCGGGAA

TACAGCTCAGTCTGCTGTGCGCTGCAGGATGTACATACATACATGCGCAG
```

The LIG3-4 target recognition site is a 22 bp polynucleotide having the following sequence:

```
(SEQ ID NO: 16)        ATATACCTC**ACAC▼GTACGCGTA**
```

The dsb site and overhang region is shown in bold, the enzyme cuts after C13, as indicated by the solid triangle.

B. LIG3-4 Meganuclease

The I-CreI meganuclease was modified to produce the LIG3-4 meganuclease designed to recognize the LIG3-4 target sequence (SEQ ID NO: 16) under contract with Precision BioSciences (Raleigh, N.C. USA). Wild-type I-CreI meganuclease is a homodimer. In order to recognize the LIG3-4 target sequence, different substitutions were made to each monomer.

i. LIG3-4 Single-Chain Fusion

The coding sequences for each monomer were joined by a linker sequence to produce a single-chain fusion polypeptide (LIG3-4SC, SEQ ID NO: 21). The amino acid substitutions are shown (bold font) in an alignment of LIG3-4 SC with wild-type I-CreI monomers (SEQ ID NO: 20).

Alignment of LIG3-4SC with Two I-CreI Wildtype Monomers:

```
                        1                                                  50
I-CreI + I-CreI         MNTKYNKEFLLYLAGFVDGDGSIIAQIKPNQSYKFKHQLSLAFQVTQKTQ
LIG3-4SC                MNTKYNKEFLLYLAGFVDGDGSIKAQIKPNQSCKFKHQLSLTFQVTQKTQ 51                                                 100
I-CreI + I-CreI         RRWFLDKLVDEIGVGYVRDRGSVSDYILSEIKPLHNFLTQLQPFLKLKQK
LIG3-4SC                RRWFLDKLVDEIGVGYVYDRGSVSDYELSQIKPLHNFLTQLQPFLKLKQK 101                                                150
I-CreI + I-CreI         QANLVLKIIWRLPSAKESPDKFLEVCTWVDQIAALNDSKTRKTTSETVRA
LIG3-4SC                QANLVLKIIEQLPSAKESPDKFLEVCTWVDQIAALNDSKTRKTTSETVRA 151                                                200
I-CreI + I-CreI         VLDSLSKKKKSSP----------------------MNTKYNKEFLLYL
LIG3-4SC                VLDSLPGSVGGLSPSQASSAASSASSSPGSGISEALRAGATKSKEFLLYL 201                                                250
I-CreI + I-CreI         AGFVDGDGSIIAQIKPNQSYKFKHQLSLAFQVTQKTQRRWFLDKLVDEIG
LIG3-4SC                AGFVDGDGSIIASIKPRQCYKFKHELRLEFTVTQKTQRRWFLDKLVDEIG
```

```
                 251                                              300
I-CreI + I-CreI  VGYVRDRGSVSDYILSEIKPLHNFLTQLQPFLKLKQKQANLVLKIIWRLP
LIG3-4SC         VGYVYDRGSVSDYRLSQIKPLHNFLTQLQPFLKLKQKQANLVLKIIEQLP 301                                              350
I-CreI + I-CreI  SAKESPDKFLEVCTWVDQIAALNDSKTRKTTSETVRAVLDSLSEKKKSSP
LIG3-4SC         SAKESPDKFLEVCTWVDQIAALNDSKTRKTTSETVRAVLDSLSEKKKSSP
``` ii. Lig3-4 Heterodimer

The coding sequences were also designed for expression of each separate monomer. Additional mutations were added to facilitate assembly of the heterodimer, rather than formation of homodimers. These mutations are noted as LIG3K (SEQ ID NO: 22), and LIG4E (SEQ ID NO: 23). The amino acid substitutions are shown (bold font) in an alignment of LIG3K and LIG4E with wild-type I-CreI monomer (SEQ ID NO: 20).

```
        1                                                 50
I-CreI  MNTKYNKEFLLYLAGFVDGDGSIIAQIKPNQSYKFKHQLSLAFQVTQKTQ
LIG3K   MNTKYNKKFLLYLAGFVDGDGSIKAQIKPNQSCKFKHQLSLTFQVTQKTQ
LIG4E   MNTKYNEEFLLYLAGFVDGDGSIIASIKPRQCYKFKHELRLEFTVTQKTQ 51                                                100
I-CreI  RRWFLDKLVDEIGVGYVRDRGSVSDYILSEIKPLHNFLTQLQPFLKLKQK
LIG3K   RRWFLDKLVDKIGVGYVYDRGSVSDYELSQIKPLHNFLTQLQPFLKLKQK
LIG4E   RRWFLDELVDEIGVGYVRDRGSVSDYRLSQIKPLHNFLTQLQPFLELKQK 101                                               150
I-CreI  QANLVLKIIWRLPSAKESPDKFLEVCTWVDQIAALNDSKTRKTTSETVRA
LIG3K   QANLVLKIIEQLPSAKESPDKFLEVCTWVDQIAALNDSKTRKTTSETVRA
LIG4E   QANLVLKIIEQLPSAKESPDKFLEVCTWVDQIAALNDSKTRKTTSETVRA

151
I-CreI  VLDSLSKKKKSSP
LIG3K   VLDSLSEKKKSSP
LIG4E   VLDSLSEKKKSSP
```

C. Transient in Planta Meganuclease Activity Assay

In order to assess the enzymatic activity of an engineered double-strand break inducing agent in a plant, a transient assay was developed. Target vectors comprising a target site and recombination substrate, and vectors comprising a double-strand break (dsb) inducing agent expression cassette were generated using standard molecular biology techniques for delivery into maize embryos.

Figure 9:
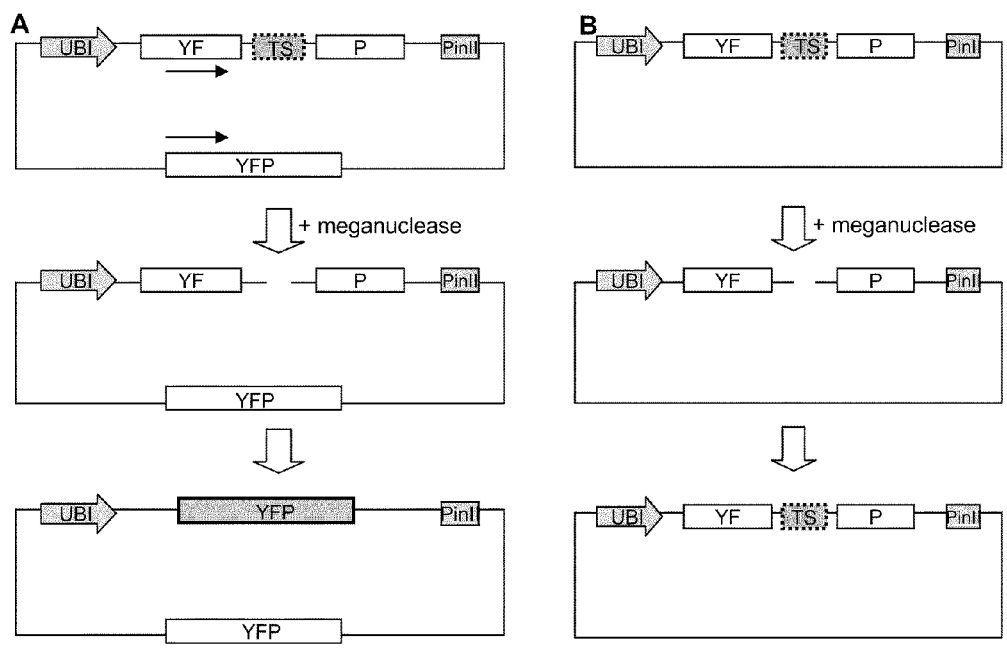
FIG. 9. Transient recombination assay in plant tissue. (A) Experimental vector for recombination assay comprising a YFP coding sequence interrupted by a double-strand break inducing agent recognition sequence (TS) and a promoterless YFP coding region in inverted orientation relative to the interrupted sequence. (B) Control vector comprising a YFP coding sequence interrupted by a double-strand break inducing agent recognition sequence (TS), but lacking a homologous YFP region.

Target vectors comprised the appropriate meganuclease recognition site cloned into a KpnI restriction enzyme site to interrupt the yellow fluorescent protein (YFP) coding region such that YFP protein is not expressed. These vectors also have a recombination repair template comprising a promoterless YFP coding region in inverted orientation (PFY) relative to the expression cassette comprising the interrupted YFP sequence (see, FIG. 9)

Target vectors include:
PHP34231 ubi pro::ubi 5' UTR::YF//I-CreI TS//P::pinII-PFY
PHP34232 ubi pro::ubi 5' UTR::YF//I-SceI TS//P::pinII-PFY
PHP34234 ubi pro::ubi 5' UTR::YF//Lig3-4 TS//P::pinII-PFY The target sequences included in the target vectors were:

```
I-CreI TS   (SEQ ID NO: 17)  CAAAACGTCGTGAGACAGTTTG
I-SceI TS   (SEQ ID NO: 2)   TAGGGATAACAGGGTAAT
LIG3-4 TS   (SEQ ID NO: 16)  ATATACCTCACACGTACGCGTA
```

Vectors comprising expression cassettes for the appropriate meganuclease were constructed using standard molecular biological techniques. Several meganucleases were tested including I-SceI, I-CreI, and LIG3-4SC. In each case, the polynucleotide encoding the meganuclease was modified to increase the usage of maize preferred codons in order to obviate possible expression problems in the plant tissue tested. The following meganuclease expression vectors were made:

PHP33978 Ubi pro::ubi 5' UTR::I-CreI::pinII
PHP33959 Ubi pro::ubi 5' UTR::I-SceI::pinII
PHP33918 Ubi pro::ubi 5' UTR::Lig3-4SC::pinII
PHP33958 Ubi pro::ubi 5' UTR::Lig3K::pinII::::: Ubi pro::ubi 5' UTR::Lig4E::pinII A YFP expression vector (PHP18096) was used as a positive control for transformation and expression:

PHP18096 ubi pro::ubi 5' UTR::YFP::pinII

For the transient assay maize immature embryos were bombarded essentially as described in Example 2A. Experimental groups included the bombardment with 100 ng YFP positive control vector (PHP18096) alone, negative controls were bombardments using the target vectors PHP34231, PHP34232, and PHP34234 alone (100 ng DNA), and treatment groups of target vector+meganuclease vector cobombardments using 100 ng of each vector for PHP34231+PHP33978, PHP34232+PHP33959, PHP34234+PHPH33918, and PHP34234+PHP33958. At 20-24 hours after bombardment, yellow spots were counted for every embryo, and results calculated for the percentage change of yellow spots for experimental treatment (target vector+meganuclease) as compared to the negative control (target vector alone). The results are shown in Table 4.

TABLE 4

| Enzyme   | % change/control ± s.d | #embryos | assay repeats |
|----------|------------------------|----------|---------------|
| I-Scel   | 194                    | 24       | 1             |
| I-Crel   | 225 ± 14.4             | 70       | 2             |
| LIG3-4SC | 43 ± 2.8               | 70       | 2             |
| LIG3-4HD | 108 ± 34               | 130      | 3             |

D. Targeted Endogenous Genomic Sequence Modifications

The strategies employed for generating and selecting genomic alterations produced do not employ reconstitution of a selectable marker expression cassette, therefore the dsb inducing agent vectors do not have a fragment of a selectable marker cassette. In this example, the dsb inducing agent vectors do have a phenotypic marker expression cassette encoding phosphinothricin acetyltransferase, which is used to validate successful delivery of the vector.

A vector containing the LIG3-4 I-CreI single chain (LIG3-4SC) coding region was constructed using standard molecular biology techniques. PHP34090 comprises the following operably linked components:
Ubi pro::ubi 5' UTR::LIG3-4SC::pinII::35S CaMV pro:: BAR::pinII
wherein ubi pro is the maize ubiquitin promoter, ubi 5' UTR is the 5' untranslated region of the maize ubiquitin gene, LIG3-4SC is an engineered I-CreI single chain meganuclease designed to specifically recognize and induce a double strand break at the endogenous LIG3-4 maize genome target site, 35S CaMV pro is the 35S Cauliflower Mosaic Virus promoter, BAR encodes phosphinothricin acetyltransferase, and pinII is the transcription termination sequence from potato proteinase inhibitor II. This vector was designed to induce double-strand breaks at the LIG3-4 target site and thereby produce alterations of the LIG3-4 target site. This vector was not constructed to produce homologous recombination events and therefore does not include regions of homology to the LIG3-4 genomic region.

A vector containing the LIG3K-4E I-CreI heterodimer (LIG3-4HD) coding regions was constructed using standard molecular biology techniques. PHP34121 comprises the following operably linked components:
Ubi pro::ubi 5' UTR::LIG3K::pinII:: Ubi pro::ubi 5' UTR:: LIG4E::pinII::35S CaMV pro::BAR::pinII
wherein ubi pro is the maize ubiquitin promoter, ubi 5' UTR is the 5' untranslated region of the maize ubiquitin gene, LIG3K and LIG4E are designed to form an engineered I-CreI nuclease heterodimer to specifically recognize and induce a double strand break at the endogenous LIG3-4 maize genome target site, 35S CaMV pro is the 35S Cauliflower Mosaic Virus promoter, BAR encodes phosphinothricin acetyltransferase, and pinII is the transcription termination sequence from potato proteinase inhibitor II. This vector was designed to induce double-strand breaks at the LIG3-4 target site and thereby produce alterations of the LIG3-4 target site. This vector was not constructed to produce homologous recombination events and therefore does not include regions of homology to the LIG3-4 genomic region.

Maize immature embryos 9-12 days after pollination (DAP) were transformed with vector PHP34090 (LIG3-4SC) or PHP34121 (LIG3-4HD) using *Agrobacterium*-mediated methods essentially as described in Example 2B1.

Successful delivery of the vectors conferred bialaphos resistance, and was used to identify putative events by callus selection on media containing 3 mg/L bialophos. Callus tissue and/or plants regenerated from stable transformants using standard culture and regeneration conditions were screened for modification(s) of the endogenous target site essentially as described in Example 5.

Transformation of maize embryos with the LIG3-4SC expression vector PHP34090 or LIG3-4HD expression vector PHP34121 each produced sequence modifications at the LIG3-4 recognition site as evidenced by PCR screening for the LIG3-4 site. Double-strand break event identification protocol did not rely on activation/inactivation of a selectable marker; instead, all bialaphos-resistant events were screened by PCR assays and/or sequencing essentially as described in Example 5 to identify and characterize events and modifications generated.

Bialaphos-resistant callus and/or T0 plant events were screened by PCR using the following LIG3-4 primer pair which is expected to produce a 536 bp product:

```
(SEQ ID NO: 18) Lig34f Biocode 136247
5' TAATTAGGGAGAGAAAAATAGAGCACCAGC;
and (SEQ ID NO: 19) Lig34r Biocode 136248
5' ATGTGCATTGCATCGCTCTTCTCTCTC
```

Figure 11:
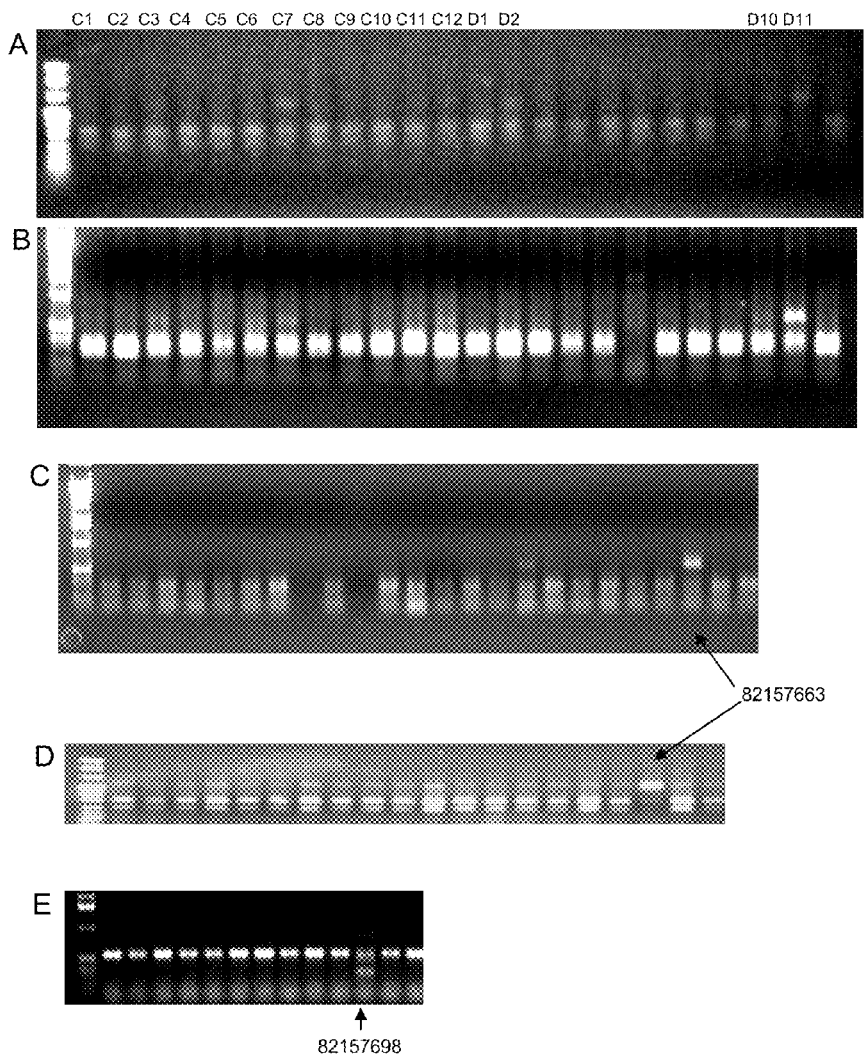
FIG. 11. Agarose gel separation of LIG3-4SC or MluI enzyme digest of LIG3-4 PCR products from putative events. (A) PCR products from PHP34090 callus samples amplified with LIG3-4 primer pair and then digested with LIG3-4SC meganuclease. (B) the same 34090 callus samples amplified with LIG3-4 primer pair and then digested with MluI. (C) PCR products from 34090 T0 plant leaf tissue amplified with the LIG3-4 primer pair and then digested with MluI, T0 plant 82157663 is indicated by the arrow. (D) PCR products from 34090 T0 plant leaf tissue amplified with the LIG3-4 primer pair and then digested with LIG3-4SC, T0 plant 82157663 is indicated by the arrow. (E) PCR products from 34090 T0 plant leaf tissue amplified with the LIG3-4 PCR primer pair for the LIG3-4 locus, T0 plant 82157698 is indicated by the arrow.

Selected samples that yielded the expected 536 bp PCR product for the LIG3-4 locus were subjected to enzyme digestion with LIG3-4SC endonuclease or MluI restriction enzyme essentially as described in Example 5D (see, FIG. 11, LIG3-4SC; FIG. 12A, LIG4-3HD). The LIG3-4 PCR product contains 2 MluI restriction enzyme recognition sites near the LIG3-4 recognition site. Products containing small modifications introduced at the LIG3-4 recognition site can still be digested by MluI, but products with larger modifications are resistant to MluI digestion (see, for example, FIG. 10, panels A and B). The MluI enzyme is commercially available and therefore provides a convenient means to identify many of the modified events.

In some cases, the LIG3-4 PCR product was directly cloned and sequenced. For example, one T0 plant event (82157698) from LIG3-4SC had a significantly smaller PCR product which was directly purified, cloned and sequenced. This event has a 220 bp deletion in the LIG3-4 target locus. (FIG. 10A, event 2)

Fourteen unique events (FIGS. 10A and B show sequence results from 12 events) comprising sequence modifications at the LIG3-4 locus have been identified and sequenced from 100 putative events using LIG3-4SC. In this experimental design, the LIG3-4 meganuclease is under control of a constitutive promoter. In some PHP34090 LIG3-4SC events, modification of the LIG3-4 locus appears to be occurring over time and cell division cycles as indicated by recovery of more than one sequence modification from some single events.

Six unique events (FIG. 12B) comprising sequence modifications at the LIG3-4 locus have been identified and sequenced from 100 putative events generated by LIG3-4HD.

T1 plants were generated from T0 plants from events 82157633 and 82157698 generated by LIG3-4SC in order to assess transmission and stability of the observed genomic modifications. The T0 plants are heterozygous for the mutation, wherein one LIG3-4 allele is mutated, and the other LIG3-4 allele is unmodified. The T0 plants were reciprocally crossed to wild type plants to produce seed. T1 seed was germinated to produce T1 seedlings and leaf samples taken for PCR analysis. T0 plant 82157633 predominantly showed a 29 bp deletion (FIG. 10A, Event 1), which was transmitted to all T1 progeny at the frequency expected. T0 plant 82157698 had a 220 bp deletion (FIG. 10A, Event 2), which was also transmitted to all T1 progeny at the frequency expected. Sequencing data indicated that the same T0 mutation was present in all progeny for each event. Therefore, once created, the genomic modification is stably transmitted to progeny at the expected segregation frequency. The results are summarized below:

| T0 ID | T0 parent | SID | Total | Wild Type | Mutant | Ratio (wt:mutant) |
|---|---|---|---|---|---|---|
| 82157633 | Male | 20593130 | 52 | 27 | 25 | 1.08 |
| 82157633 | Male | 20593131 | 51 | 28 | 23 | 1.22 |
| 82157633 | Male | 20593135 | 48 | 23 | 25 | 0.92 |
| 82157633 | Female | 20621694 | 48 | 24 | 24 | 1.00 |
| 82157698 | Male | 20593132 | 56 | 24 | 32 | 0.75 |
| 82157698 | Male | 20593133 | 55 | 25 | 30 | 0.83 |
| 82157698 | Female | 20621692 | 59 | 28 | 31 | 0.90 |

T1 progeny from 82157633 and 82157698 were also evaluated for segregation of the T-DNA and the genomic mutation by PCR analyses for the BAR gene on the LIG3-4SC vector (PHP34090), and for the mutated LIG3-4 allele. Four patterns were expected and observed: no mutation (mut−), BAR positive (BAR+); no mutation, BAR negative (BAR−); mutation (mut+), BAR negative; and mutation, BAR positive. As expected, the targeting vector T-DNA segregated independently of the genomic mutation. Therefore, progeny containing only the genomic modification can be selected (mut+, BAR−). The results of this analysis are summarized below:

|  | 82157663 | | | | 82157698 | | |
|---|---|---|---|---|---|---|---|
|  | 20593130 | 20593131 | 20593135 | 20621694 | 20593132 | 20593133 | 20621692 |
| mut−Bar+ | 9 | 13 | 12 | 13 | 23 | 21 | 19 |
| mut−Bar− | 15 | 15 | 12 | 17 | 1 | 4 | 5 |
| mut+bar− | 13 | 14 | 9 | 12 | 5 | 6 | 9 |
| mut+Bar+ | 15 | 9 | 17 | 11 | 27 | 25 | 25 |
| Bar+ | 24 | 22 | 29 | 24 | 50 | 46 | 44 |
| Bar− | 28 | 29 | 21 | 29 | 6 | 10 | 14 |

Example 7

As an alternative to re-transformation, any component of the modification system can be provided by sexual crossing.

Figure 13:
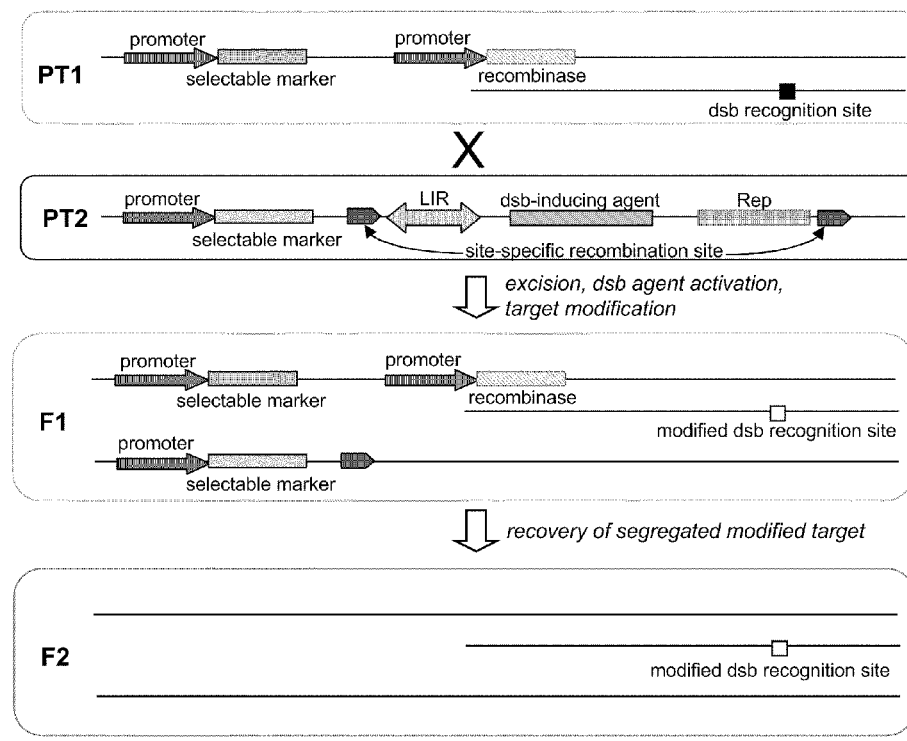
FIG. 13. Examplary crossing strategy genome modification. PT1 is a first parental transgenic plant. PT2 is a second parental transgenic plant.

In this example, the crossing strategy can be used to control the activation & expression of the double-strand break agent by using the replicon system described in Example 1B4 and in FIG. 13. Briefly, transgenic parental line 1 (PT1) comprises a target dsb recognition site and a site-specific recombinase expression cassette. The target dsb recognition site can be an artificial target site such as ATS2, or an endogenous site such as LIG34. Transgenic parental line 2 (PT2) comprises a double-strand break inducing agent expression replicon flanked by excision sites for the site-specific recombinase. Crossing PT1 and PT2 results in excision of the replicon by recombinase, activation of expression of the dsb agent and replicase (Rep), dsb generation, and modification of the target dsb recognition site. Further outcrossing can be used to segregate the modified target site away from the other remnants of the system.

Figure 14:
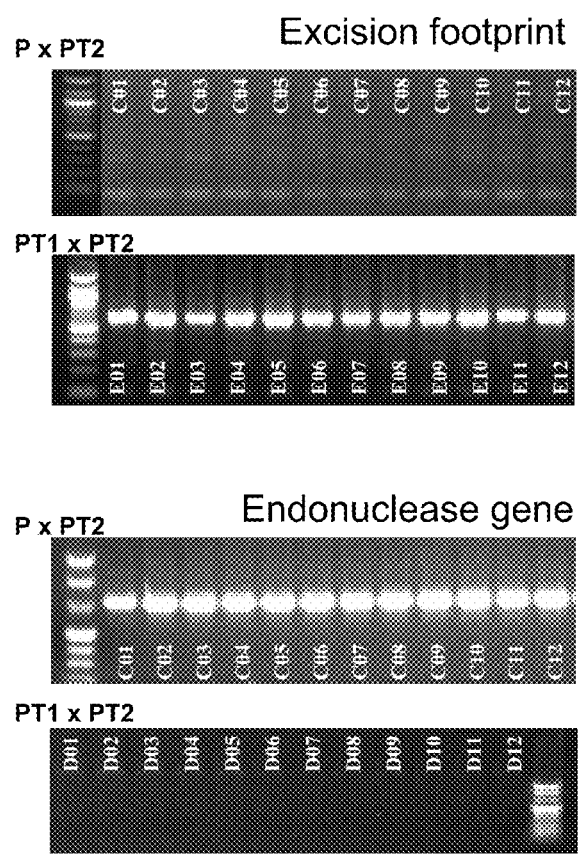
FIG. 14. PCR screening of F1 progeny of control and experimental crosses for presence of excision footprint or endonuclease gene. PT1 is a first parental transgenic plant. PT2 is a second parental transgenic plant. P is a non-transgenic parental plant.
Figure 15:
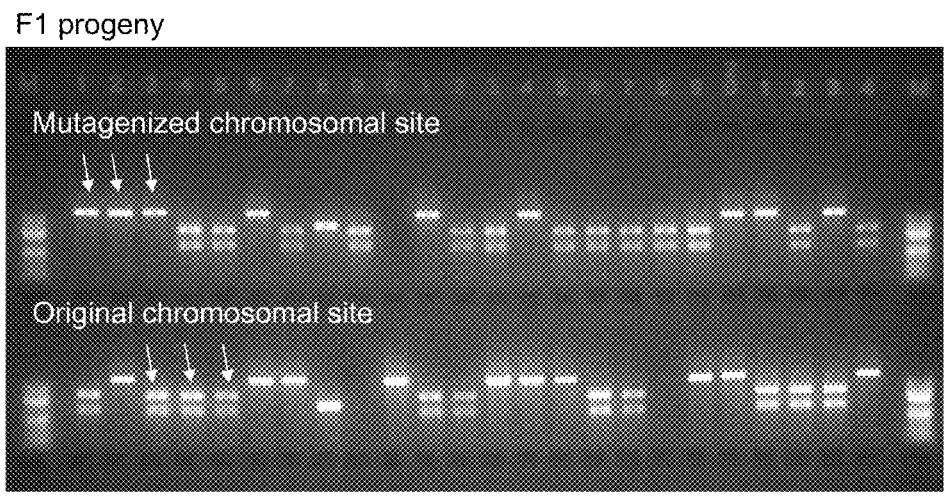
FIG. 15. PCR-based screen of F1 progeny for modified target sites. PCR amplified fragments from putative events were run on agarose gels after digestion with I-SceI endonuclease. Intact I-SceI sites should produce two fragments, while modified sites should make the fragments refractory to digestion.

This strategy was tested using hemizygous maize lines (PT1) comprising an introduced I-SceI recognition sequence flanking by regions of homology (ATS2) that were produced as described in Example 4. Parental transgenic line 2 comprised PHP28184 as described in Example 1B4. Reciprocal crosses were made between PT1 and PT2 lines. Crosses of PT1 or PT2 to a non-transgenic line (P) were used as controls, for example in PCR assays for the excision footprint or endonuclease gene (FIG. 14). As seen in FIG. 14, progeny from a control cross of PT2×P are negative for the excision footprint, while the PT1×PT2 crosses show the expected excision footprint product. Additionally, the PT2×P control cross shows the retention of the endonuclease gene in the progeny, while the PT1×PT2 crosses show that the endonuclease gene is excised and not transmitted to the progeny. This provides a convenient system to both control activation of endonuclease expression, but also to eliminate transmission of the endonuclease gene to later generations. Progeny of the PT1×PT2 crosses were screened for target modification as described in Examples 1 and 5 for presence and/or change in ATS2, sensitivity to I-SceI endonuclease digestion (FIG. 15), and sequence analysis of ATS2 and junctions (FIG. 16).

The frequency of mutation observed in the F1 progeny did show a bias depending on which plant, PT1 or PT2, was used as the female parent in the cross. However, more constructs and data may be needed before definitive conclusions can be drawn regarding bias observed from this one set of data. These results are summarized below:

| Female | Male | Seeds | Mutations | Mutation Rate (%) |
|---|---|---|---|---|
| PT2 | PT1 | 1001 | 0 | 0.00 |
| PT1 | PT2 | 2805 | 40 | 1.41 |

What is claimed is:

1. A method of modifying a specific endogenous genomic target sequence comprising:
   (a) contacting at least one monocot plant cell comprising the endogenous genomic target sequence in its genome with (i) a phenotypic marker, (ii) a DNA fragment, and (iii) an engineered double-strand break inducing agent capable of inducing a double-strand break at the endogenous genomic target sequence, wherein the engineered double-strand break inducing agent comprises SEQ ID NO:21;
   (b) selecting cells comprising the phenotypic marker wherein the phenotypic marker is not indicative of integration at the endogenous genomic target sequence; and
   (c) identifying cells from step (b) having an alteration in their genome at the endogenous genomic target sequence wherein the alteration is selected from the group consisting of (i) replacement of at least one nucleotide, (ii) a deletion of at least one nucleotide, (iii) an insertion of at least one nucleotide, and (iv) any combination of (i)-(iii),
   wherein identifying comprises any method that does not use the phenotypic marker.

2. The method of claim 1, wherein the monocot plant cell is from maize, rice, sorghum, barley, wheat, millet, oats, sugarcane, turfgrass, or switch grass.

3. The method of claim 1, wherein the monocot plant cell is from maize.

4. The method of claim 1, further comprising recovering a fertile monocot plant having the alteration in its genome.

* * * * *

SEQUENCE LISTING

<160> NUMBER OF SEQ ID NOS: 23

<210> SEQ ID NO 1
<211> LENGTH: 720
<212> TYPE: DNA
<213> ORGANISM: Artificial Sequence
<220> FEATURE:
<223> OTHER INFORMATION: Maize codon-modified I-SceI coding sequence (moI-SceI)

<400> SEQUENCE: 1

```
atggccaaga acatcaagaa gaaccaggtg atgaacctgg ccccgaacag caagctcctg      60
aaggagtaca agtcgcagct catcgagctg aacatcgagc agttcgaggc cggcatcggc     120
ctcatcctgg gcgacgccta catcaggtcc cgcgacgagg gcaagaccta ctgcatgcag     180
ttcgagtgga agaacaaggc gtacatggac cacgtgtgcc tcctgtacga ccagtgggtc     240
ctcagcccgc cgcacaagaa ggagcgcgtg aaccacctgg caacctcgt catcacgtgg      300
ggcgcccaga ccttcaagca ccaggcgttc aacaagctgg ccaacctctt catcgtgaac     360
aacaagaaga cgatcccgaa caacctggtc gagaactacc tcacgcccat gtcgctggcg     420
tactggttca tggacgacgg cggcaagtgg gactacaaca gaactccac gaacaagagc      480
atcgtgctca cacccagtc gttcacgttc gaggaggtcg agtacctggt gaagggcctc      540
cggaacaagt tccagctcaa ctgctacgtc aagatcaaca gaacaagcc gatcatctac      600
atcgactcca tgagctacct catcttctac aacctgatca gccctacct catcccgcag      660
atgatgtaca agctgcccaa caccatctcg tccgagacgt tcctcaaggc cgcggactga     720
```

<210> SEQ ID NO 2
<211> LENGTH: 18
<212> TYPE: DNA
<213> ORGANISM: Saccharomyces cerevisiae
<220> FEATURE:
<221> NAME/KEY: misc_feature
<222> LOCATION: (1)...(18)
<223> OTHER INFORMATION: I-SceI recognition sequence

<400> SEQUENCE: 2

```
tagggataac agggtaat                                                    18
```

<210> SEQ ID NO 3
<211> LENGTH: 25
<212> TYPE: DNA
<213> ORGANISM: Artificial Sequence
<220> FEATURE:
<223> OTHER INFORMATION: ATS primer 104797

<400> SEQUENCE: 3

```
tcgtgaacca ctacatcgcg acctc                                            25
```

<210> SEQ ID NO 4
<211> LENGTH: 23
<212> TYPE: DNA
<213> ORGANISM: Artificial Sequence
<220> FEATURE:
<223> OTHER INFORMATION: ATS primer 104798

<400> SEQUENCE: 4

```
agcagcttgt gctggatgaa gtg                                              23
```

<210> SEQ ID NO 5
<211> LENGTH: 20
<212> TYPE: DNA

```
<213> ORGANISM: Artificial Sequence
<220> FEATURE:
<223> OTHER INFORMATION: I-SceI primer 59723

<400> SEQUENCE: 5
tcttgctggg cacgctcttg                                              20

<210> SEQ ID NO 6
<211> LENGTH: 25
<212> TYPE: DNA
<213> ORGANISM: Artificial Sequence
<220> FEATURE:
<223> OTHER INFORMATION: I-Sce1 primer 104381

<400> SEQUENCE: 6
ggtctcgatc tttggccttg gtagt                                        25

<210> SEQ ID NO 7
<211> LENGTH: 33
<212> TYPE: DNA
<213> ORGANISM: Artificial Sequence
<220> FEATURE:
<223> OTHER INFORMATION: HR primer 124641

<400> SEQUENCE: 7
taagattaaa atagctttcc cccgttgcag cgc                               33

<210> SEQ ID NO 8
<211> LENGTH: 23
<212> TYPE: DNA
<213> ORGANISM: Artificial Sequence
<220> FEATURE:
<223> OTHER INFORMATION: HR primer 104798

<400> SEQUENCE: 8
agcagcttgt gctggatgaa gtg                                          23

<210> SEQ ID NO 9
<211> LENGTH: 26
<212> TYPE: DNA
<213> ORGANISM: Artificial Sequence
<220> FEATURE:
<223> OTHER INFORMATION: LB primer 104801

<400> SEQUENCE: 9
ttcgaagatc tgcccactag tgagtc                                       26

<210> SEQ ID NO 10
<211> LENGTH: 23
<212> TYPE: DNA
<213> ORGANISM: Artificial Sequence
<220> FEATURE:
<223> OTHER INFORMATION: LB primer 104798

<400> SEQUENCE: 10
agcagcttgt gctggatgaa gtg                                          23

<210> SEQ ID NO 11
<211> LENGTH: 25
<212> TYPE: DNA
<213> ORGANISM: Artificial Sequence
<220> FEATURE:
<223> OTHER INFORMATION: LB primer 104381

<400> SEQUENCE: 11
ggtctcgatc tttggccttg gtagt                                        25
```

<210> SEQ ID NO 12
<211> LENGTH: 30
<212> TYPE: DNA
<213> ORGANISM: Artificial Sequence
<220> FEATURE:
<223> OTHER INFORMATION: LB primer 124437

<400> SEQUENCE: 12
cttgttgaac gcctggtgct tgaaggtctg                              30

<210> SEQ ID NO 13
<211> LENGTH: 30
<212> TYPE: DNA
<213> ORGANISM: Artificial Sequence
<220> FEATURE:
<223> OTHER INFORMATION: RB primer 124437

<400> SEQUENCE: 13
cttgttgaac gcctggtgct tgaaggtctg                              30

<210> SEQ ID NO 14
<211> LENGTH: 23
<212> TYPE: DNA
<213> ORGANISM: Artificial Sequence
<220> FEATURE:
<223> OTHER INFORMATION: RB primer 104798

<400> SEQUENCE: 14
agcagcttgt gctggatgaa gtg                                     23

<210> SEQ ID NO 15
<211> LENGTH: 200
<212> TYPE: DNA
<213> ORGANISM: Zea mays
<220> FEATURE:
<221> NAME/KEY: misc_feature
<222> LOCATION: (0)...(0)
<223> OTHER INFORMATION: LIG3-4 genomic target locus

<400> SEQUENCE: 15
cttcttttga tcggctgcgg aaataatata ctgtaacgat ttacgcacct gctgggaatt    60
gtaccgtacg tgccccggcg gaggatatat ataccctcaca cgtacgcgta cgcgtatata  120
tacgtgcgct gctactcatt tgcgcgggaa tacagctcag tctgctgtgc gctgcaggat  180
gtacatacat acatgcgcag                                              200

<210> SEQ ID NO 16
<211> LENGTH: 22
<212> TYPE: DNA
<213> ORGANISM: Zea mays
<220> FEATURE:
<221> NAME/KEY: misc_feature
<222> LOCATION: (0)...(0)
<223> OTHER INFORMATION: LIG3-4 recognition sequence

<400> SEQUENCE: 16
atatacctca cacgtacgcg ta                                      22

<210> SEQ ID NO 17
<211> LENGTH: 22
<212> TYPE: DNA
<213> ORGANISM: Chlamydomonas reinhardtii
<220> FEATURE:
<221> NAME/KEY: misc_feature
<222> LOCATION: (0)...(0)

```
<223> OTHER INFORMATION: I-CreI recognition sequence

<400> SEQUENCE: 17
caaaacgtcg tgagacagtt tg                                            22

<210> SEQ ID NO 18
<211> LENGTH: 29
<212> TYPE: DNA
<213> ORGANISM: Artificial Sequence
<220> FEATURE:
<223> OTHER INFORMATION: Primer Lig34f Biocode 136247

<400> SEQUENCE: 18
taattaggga gagaaaaata gagcaccag                                     29

<210> SEQ ID NO 19
<211> LENGTH: 27
<212> TYPE: DNA
<213> ORGANISM: Artificial Sequence
<220> FEATURE:
<223> OTHER INFORMATION: Primer Lig34r Biocode 136248

<400> SEQUENCE: 19
atgtgcattg catcgctctt ctctctc                                       27

<210> SEQ ID NO 20
<211> LENGTH: 163
<212> TYPE: PRT
<213> ORGANISM: Chlamydomonas reinhardtii
<220> FEATURE:
<223> OTHER INFORMATION: I-CreI monomer

<400> SEQUENCE: 20

Met Asn Thr Lys Tyr Asn Lys Glu Phe Leu Leu Tyr Leu Ala Gly Phe
 1               5                  10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Lys Lys Lys Lys
145                 150                 155                 160

Ser Ser Pro

<210> SEQ ID NO 21
<211> LENGTH: 350
<212> TYPE: PRT
<213> ORGANISM: Artificial Sequence
```

<220> FEATURE:
<223> OTHER INFORMATION: LIG3-4 single chain custom meganuclease

<400> SEQUENCE: 21

```
Met Asn Thr Lys Tyr Asn Lys Glu Phe Leu Leu Tyr Leu Ala Gly Phe
1               5                   10                  15

Val Asp Gly Asp Gly Ser Ile Lys Ala Gln Ile Lys Pro Asn Gln Ser
            20                  25                  30

Cys Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Arg Gly Ser Val Ser Asp Tyr Glu Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Thr Lys
            180                 185                 190

Ser Lys Glu Phe Leu Leu Tyr Leu Ala Gly Phe Val Asp Gly Asp Gly
        195                 200                 205

Ser Ile Ile Ala Ser Ile Lys Pro Arg Gln Cys Tyr Lys Phe Lys His
    210                 215                 220

Glu Leu Arg Leu Glu Phe Thr Val Thr Gln Lys Thr Gln Arg Arg Trp
225                 230                 235                 240

Phe Leu Asp Lys Leu Val Asp Glu Ile Gly Val Gly Tyr Val Tyr Asp
                245                 250                 255

Arg Gly Ser Val Ser Asp Tyr Arg Leu Ser Gln Ile Lys Pro Leu His
            260                 265                 270

Asn Phe Leu Thr Gln Leu Gln Pro Phe Leu Lys Leu Lys Gln Lys Gln
        275                 280                 285

Ala Asn Leu Val Leu Lys Ile Ile Glu Gln Leu Pro Ser Ala Lys Glu
    290                 295                 300

Ser Pro Asp Lys Phe Leu Glu Val Cys Thr Trp Val Asp Gln Ile Ala
305                 310                 315                 320

Ala Leu Asn Asp Ser Lys Thr Arg Lys Thr Thr Ser Glu Thr Val Arg
                325                 330                 335

Ala Val Leu Asp Ser Leu Ser Glu Lys Lys Lys Ser Ser Pro
            340                 345                 350
```

<210> SEQ ID NO 22
<211> LENGTH: 163
<212> TYPE: PRT
<213> ORGANISM: Artificial Sequence
<220> FEATURE:
<223> OTHER INFORMATION: LIG3K nuclease monomer derived by modification of I-CreI endonuclease

```
<400> SEQUENCE: 22

Met Asn Thr Lys Tyr Asn Lys Lys Phe Leu Leu Tyr Leu Ala Gly Phe
 1               5                  10                  15

Val Asp Gly Asp Gly Ser Ile Lys Ala Gln Ile Lys Pro Asn Gln Ser
             20                  25                  30

Cys Lys Phe Lys His Gln Leu Ser Leu Thr Phe Gln Val Thr Gln Lys
         35                  40                  45

Thr Gln Arg Arg Trp Phe Leu Asp Lys Leu Val Asp Lys Ile Gly Val
     50                  55                  60

Gly Tyr Val Tyr Asp Arg Gly Ser Val Ser Asp Tyr Glu Leu Ser Gln
 65                  70                  75                  80

Ile Lys Pro Leu His Asn Phe Leu Thr Gln Leu Gln Pro Phe Leu Lys
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Ser Glu Lys Lys Lys
145                 150                 155                 160

Ser Ser Pro

<210> SEQ ID NO 23
<211> LENGTH: 163
<212> TYPE: PRT
<213> ORGANISM: Artificial Sequence
<220> FEATURE:
<223> OTHER INFORMATION: LIG4E nuclease monomer derived by modification
      of I-CreI endonuclease

<400> SEQUENCE: 23

Met Asn Thr Lys Tyr Asn Glu Glu Phe Leu Leu Tyr Leu Ala Gly Phe
 1               5                  10                  15

Val Asp Gly Asp Gly Ser Ile Ile Ala Ser Ile Lys Pro Arg Gln Cys
             20                  25                  30

Tyr Lys Phe Lys His Glu Leu Arg Leu Glu Phe Thr Val Thr Gln Lys
         35                  40                  45

Thr Gln Arg Arg Trp Phe Leu Asp Glu Leu Val Asp Glu Ile Gly Val
     50                  55                  60

Gly Tyr Val Arg Asp Arg Gly Ser Val Ser Asp Tyr Arg Leu Ser Gln
 65                  70                  75                  80

Ile Lys Pro Leu His Asn Phe Leu Thr Gln Leu Gln Pro Phe Leu Glu
                 85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
130                 135                 140

Ser Glu Thr Val Arg Ala Val Leu Asp Ser Leu Ser Glu Lys Lys Lys
145                 150                 155                 160

Ser Ser Pro
```